(12) United States Patent
Patel et al.

(10) Patent No.: US 12,144,624 B2
(45) Date of Patent: *Nov. 19, 2024

(54) SYSTEMS AND METHODS FOR PLASMA COLLECTION

(71) Applicant: FENWAL, INC., Lake Zurich, IL (US)

(72) Inventors: Amit J. Patel, Algonquin, IL (US);
Samantha M. Planas, Wauconda, IL (US); Walter T. Watts, Lake Forest, IL (US); Kyungyoon Min, Kildeer, IL (US); Daniel R. Boggs, Libertyville, IL (US); Katherine N. Radwanski, Highland Park, IL (US)

(73) Assignee: FENWAL, INC., Lake Zurich, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/371,795

(22) Filed: Sep. 22, 2023

(65) Prior Publication Data
US 2024/0023855 A1  Jan. 25, 2024

Related U.S. Application Data

(63) Continuation of application No. 17/861,437, filed on Jul. 11, 2022, now Pat. No. 11,801,001, which is a
(Continued)

(51) Int. Cl.
*A61B 5/15* (2006.01)

(52) U.S. Cl.
CPC .. *A61B 5/150992* (2013.01); *A61B 5/150229* (2013.01); *A61B 5/150251* (2013.01); *A61B 5/150343* (2013.01); *A61B 2560/0487* (2013.01)

(58) Field of Classification Search
CPC .. A61M 1/265; A61M 1/3496; A61M 1/3609; A61M 1/3693; A61M 1/38;
(Continued)

(56) References Cited

U.S. PATENT DOCUMENTS

| 1,025,059 A | 4/1912 | Joseph et al. |
| 1,611,725 A | 12/1926 | Degerth et al. |

(Continued)

FOREIGN PATENT DOCUMENTS

| CN | 2735985 Y | 10/2005 |
| CN | 102046223 A | 5/2011 |

(Continued)

OTHER PUBLICATIONS

1 Supplementary European Search Report, App. No. 21883480.2, dated Jan. 25, 2024, 8 pages.
(Continued)

*Primary Examiner* — Benjamin S Melhus
*Assistant Examiner* — Severo Antonio P Lopez
(74) *Attorney, Agent, or Firm* — Becker Patent Law, LLC

(57) ABSTRACT

A plasmapheresis system and a method for operating a plasmapheresis system are provided by which a volume of plasma product (i.e., anticoagulated plasma) so that that the targeted volume of pure plasma in the plasma product is determined based on donor-specific characteristics. In particular, the targeted amount of pure plasma to be collected is based on the weight, or the weight and the height, of the donor. The targeted volume of pure plasma to be collected, TVP, may be a multiple of the donors weight. Alternatively, TVP may be a multiple of the donor's total blood volume, TBV, with the TBV of the donor being determined based on the donor's weight and height. A target volume for the plasma product to be collected, TVPP, is established, and separation of whole blood into a plasma component and a second component continues until the volume of plasma product in a collection container equals TVPP.

8 Claims, 12 Drawing Sheets

Related U.S. Application Data continuation of application No. 17/306,099, filed on May 3, 2021, now Pat. No. 11,412,967, which is a continuation-in-part of application No. 16/739,441, filed on Jan. 10, 2020, now Pat. No. 11,383,013, which is a continuation of application No. PCT/US2019/033318, filed on May 21, 2019.

(60) Provisional application No. 63/140,534, filed on Jan. 22, 2021, provisional application No. 62/846,400, filed on May 10, 2019, provisional application No. 62/752,480, filed on Oct. 30, 2018, provisional application No. 62/674,144, filed on May 21, 2018.

(58) Field of Classification Search
CPC .......... A61M 1/385; A61M 2202/0415; A61M 2205/3379; A61M 2205/3393; A61M 2230/207
See application file for complete search history.

(56) References Cited

U.S. PATENT DOCUMENTS

| | | |
|---|---|---|
| 2,087,778 A | 7/1937 | Nelin |
| 2,661,150 A | 12/1953 | Abbott, Jr. |
| 2,750,107 A | 6/1956 | More |
| 2,792,172 A | 5/1957 | Tait |
| 3,096,283 A | 7/1963 | Hein |
| 3,145,713 A | 8/1964 | Latham |
| 3,239,136 A | 3/1966 | Hein |
| 3,244,362 A | 4/1966 | Hein |
| 3,244,363 A | 4/1966 | Hein |
| 3,409,213 A | 11/1968 | Latham |
| 3,456,875 A | 7/1969 | Hein |
| 3,489,145 A | 1/1970 | Judson et al. |
| 3,565,330 A | 2/1971 | Allen |
| 3,655,058 A | 4/1972 | Novak |
| 3,737,096 A | 6/1973 | Jones et al. |
| 3,774,840 A | 11/1973 | Boatright |
| 3,987,961 A | 10/1976 | Sinn et al. |
| 4,007,871 A | 2/1977 | Jones et al. |
| 4,010,894 A | 3/1977 | Kellogg et al. |
| 4,014,497 A | 3/1977 | Spiewok et al. |
| 4,040,965 A | 8/1977 | Kohlheb |
| 4,056,224 A | 11/1977 | Lolachi |
| 4,082,217 A | 4/1978 | Westberg |
| 4,086,925 A | 5/1978 | Dodge |
| 4,140,268 A | 2/1979 | Lacour |
| 4,142,670 A | 3/1979 | Ishimaru et al. |
| 4,151,844 A | 5/1979 | Almond et al. |
| 4,197,847 A | 4/1980 | Djerassi |
| 4,285,464 A | 8/1981 | Latham |
| 4,300,717 A | 11/1981 | Latham |
| 4,303,193 A | 12/1981 | Latham |
| 4,321,921 A | 3/1982 | Laszczower |
| 4,387,848 A | 6/1983 | Kellogg et al. |
| 4,425,114 A | 1/1984 | Schoendorfer et al. |
| 4,430,072 A | 2/1984 | Kellogg et al. |
| 4,447,221 A | 5/1984 | Mulzet |
| 4,457,747 A | 7/1984 | Tu |
| 4,464,167 A | 8/1984 | Schoendorfer et al. |
| 4,466,888 A | 8/1984 | Verkaart |
| 4,482,342 A | 11/1984 | Lueptow et al. |
| 4,490,135 A | 12/1984 | Troutner |
| 4,530,691 A | 7/1985 | Brown |
| 4,534,863 A | 8/1985 | Bacon et al. |
| 4,643,714 A | 2/1987 | Brose |
| 4,647,279 A | 3/1987 | Mulzet et al. |
| 4,655,742 A | 4/1987 | Vantard |
| 4,680,025 A | 7/1987 | Kruger et al. |
| 4,684,361 A | 8/1987 | Feldman et al. |
| 4,692,136 A | 9/1987 | Feldman et al. |
| 4,708,712 A | 11/1987 | Mulzet |
| 4,713,176 A | 12/1987 | Schoendorfer et al. |
| 4,734,089 A | 3/1988 | Cullis |
| 4,740,202 A | 4/1988 | Stacey et al. |
| 4,740,313 A | 4/1988 | Schoendorfer et al. |
| 4,755,300 A | 7/1988 | Fischel et al. |
| 4,767,396 A | 8/1988 | Powers |
| 4,795,419 A | 1/1989 | Yawn et al. |
| 4,795,448 A | 1/1989 | Stacey et al. |
| 4,806,247 A | 2/1989 | Schoendorfer et al. |
| 4,806,252 A | 2/1989 | Brown et al. |
| 4,808,307 A | 2/1989 | Fischel et al. |
| 4,850,995 A | 7/1989 | Tie et al. |
| 4,869,812 A | 9/1989 | Schoendorfer et al. |
| 4,871,462 A | 10/1989 | Fischel et al. |
| 4,876,013 A | 10/1989 | Shmidt et al. |
| 4,889,524 A | 12/1989 | Fell et al. |
| 4,898,675 A | 2/1990 | Lavender |
| 4,911,833 A | 3/1990 | Schoendorfer et al. |
| 4,934,995 A | 6/1990 | Cullis |
| 4,940,543 A | 7/1990 | Brown et al. |
| 4,943,273 A | 7/1990 | Pages |
| 4,968,295 A | 11/1990 | Neumann |
| 4,980,054 A | 12/1990 | Lavender |
| 4,983,156 A | 1/1991 | Knelson |
| 4,983,158 A | 1/1991 | Headley |
| 4,985,153 A | 1/1991 | Kuroda et al. |
| 4,994,188 A | 2/1991 | Prince |
| 5,039,401 A | 8/1991 | Columbus et al. |
| 5,045,048 A | 9/1991 | Kaleskas et al. |
| 5,098,372 A | 3/1992 | Jonsson |
| 5,098,373 A | 3/1992 | Polaschegg |
| 5,100,372 A | 3/1992 | Headley |
| 5,100,564 A | 3/1992 | Pall et al. |
| 5,112,298 A | 5/1992 | Prince et al. |
| 5,114,396 A | 5/1992 | Unger et al. |
| 5,135,667 A | 8/1992 | Schoendorfer |
| 5,141,486 A | 8/1992 | Antwiler et al. |
| 5,147,290 A | 9/1992 | Jonsson |
| 5,154,716 A | 10/1992 | Bauman et al. |
| 5,174,894 A | 12/1992 | Ohsawa et al. |
| 5,178,603 A | 1/1993 | Prince |
| 5,194,145 A | 3/1993 | Schoendorfer |
| 5,217,426 A | 6/1993 | Bacehowski et al. |
| 5,217,427 A | 6/1993 | Cullis |
| 5,234,403 A | 8/1993 | Yoda et al. |
| 5,254,248 A | 10/1993 | Nakamura |
| 5,273,517 A | 12/1993 | Barone et al. |
| 5,277,701 A | 1/1994 | Christie et al. |
| 5,298,016 A | 3/1994 | Gordon |
| 5,298,171 A | 3/1994 | Biesel |
| 5,300,060 A | 4/1994 | Nelson |
| 5,316,540 A | 5/1994 | Mcmannis et al. |
| 5,318,511 A | 6/1994 | Riquier et al. |
| 5,318,512 A | 6/1994 | Neumann |
| 5,348,533 A | 9/1994 | Papillon et al. |
| 5,368,542 A | 11/1994 | Mcmannis et al. |
| 5,368,555 A | 11/1994 | Sussman et al. |
| 5,386,734 A | 2/1995 | Pusinelli |
| 5,387,174 A | 2/1995 | Rochat |
| 5,387,187 A | 2/1995 | Fell et al. |
| 5,403,272 A | 4/1995 | Deniega et al. |
| 5,405,308 A | 4/1995 | Headley et al. |
| 5,417,650 A | 5/1995 | Gordon |
| 5,431,814 A | 7/1995 | Jorgensen |
| 5,437,598 A | 8/1995 | Delbert |
| 5,437,624 A | 8/1995 | Langley |
| 5,462,667 A | 10/1995 | Wollinsky et al. |
| 5,470,483 A | 11/1995 | Bene et al. |
| 5,484,396 A | 1/1996 | Naficy |
| 5,494,592 A | 2/1996 | Latham et al. |
| 5,496,265 A | 3/1996 | Langley et al. |
| 5,505,685 A | 4/1996 | Delbert |
| 5,514,070 A | 5/1996 | Pages |
| 5,543,062 A | 8/1996 | Nishimura |
| 5,551,941 A | 9/1996 | Howell |
| 5,585,007 A | 12/1996 | Antanavich et al. |
| 5,607,579 A | 3/1997 | Latham et al. |
| 5,649,903 A | 7/1997 | Deniega et al. |
| 5,651,766 A | 7/1997 | Kingsley et al. |
| 5,656,163 A | 8/1997 | Brown |
| 5,665,061 A | 9/1997 | Antwiler |

(56) References Cited

U.S. PATENT DOCUMENTS

| | | |
|---|---|---|
| 5,681,273 A | 10/1997 | Brown |
| 5,686,696 A | 11/1997 | Baker, Jr. et al. |
| 5,712,798 A | 1/1998 | Langley et al. |
| 5,728,060 A | 3/1998 | Kingsley et al. |
| 5,733,253 A | 3/1998 | Headley et al. |
| 5,733,446 A | 3/1998 | Holm |
| 5,733,545 A | 3/1998 | Hood, III |
| 5,738,792 A | 4/1998 | Schoendorfer |
| 5,762,791 A | 6/1998 | Deniega et al. |
| 5,779,660 A | 7/1998 | Kingsley et al. |
| 5,783,085 A | 7/1998 | Fischel |
| 5,792,351 A | 8/1998 | Wehrle et al. |
| 5,849,203 A | 12/1998 | Brown et al. |
| 5,882,289 A | 3/1999 | Sakota et al. |
| 5,906,589 A | 5/1999 | Gordon et al. |
| 5,919,125 A | 7/1999 | Berch |
| 5,964,724 A | 10/1999 | Rivera et al. |
| 5,970,432 A | 10/1999 | Ishimoto et al. |
| 5,980,760 A | 11/1999 | Min et al. |
| 6,007,725 A | 12/1999 | Brown |
| 6,059,979 A | 5/2000 | Brown |
| 6,080,322 A | 6/2000 | Deniega et al. |
| 6,183,651 B1 | 2/2001 | Brown et al. |
| 6,200,287 B1 | 3/2001 | Keller et al. |
| 6,204,694 B1 | 3/2001 | Sunter et al. |
| 6,207,063 B1 | 3/2001 | Brown |
| 6,234,989 B1 | 5/2001 | Brierton et al. |
| 6,251,284 B1 | 6/2001 | Bischof et al. |
| 6,284,142 B1 | 9/2001 | Muller |
| 6,287,818 B1 | 9/2001 | Kazimir et al. |
| 6,296,602 B1 | 10/2001 | Headley |
| 6,325,775 B1 | 12/2001 | Thom et al. |
| 6,348,156 B1 | 2/2002 | Vishnoi et al. |
| 6,405,508 B1 | 6/2002 | Janesky |
| 6,464,624 B2 | 10/2002 | Pages |
| 6,471,855 B1 | 10/2002 | Odak |
| 6,497,676 B1 | 12/2002 | Childers et al. |
| 6,558,307 B2 | 5/2003 | Headley |
| 6,623,443 B1 | 9/2003 | Polaschegg |
| 6,641,552 B1 | 11/2003 | Kingsley et al. |
| 6,695,806 B2 | 2/2004 | Gelfand et al. |
| 6,730,054 B2 | 5/2004 | Pierce et al. |
| 6,730,055 B2 | 5/2004 | Bainbridge et al. |
| 6,743,192 B1 | 6/2004 | Sakota et al. |
| 6,746,547 B2 | 6/2004 | Cole et al. |
| 6,983,884 B2 | 1/2006 | Auchlinleck |
| 7,050,611 B2 | 5/2006 | Bodicker et al. |
| 7,072,769 B2 | 7/2006 | Fletcher-Haynes et al. |
| 7,115,205 B2 | 10/2006 | Robinson et al. |
| 7,186,231 B2 | 3/2007 | Takagi et al. |
| 7,270,645 B2 | 9/2007 | Langley et al. |
| 7,282,154 B2 | 10/2007 | Muller |
| 7,354,415 B2 | 4/2008 | Bainbridge et al. |
| 7,476,209 B2 | 1/2009 | Gara et al. |
| 7,704,454 B1 | 4/2010 | Langley et al. |
| 8,628,489 B2 | 1/2014 | Pages et al. |
| 8,702,637 B2 | 4/2014 | Pages et al. |
| 8,759,094 B2 | 6/2014 | Ranby et al. |
| 8,840,790 B2 | 9/2014 | Wegener et al. |
| 9,011,359 B2 | 4/2015 | Wegener et al. |
| 9,095,665 B2 | 8/2015 | Pagès et al. |
| 9,283,316 B2 | 3/2016 | Flexman |
| 9,302,042 B2 | 4/2016 | Pages et al. |
| 9,364,600 B2 | 6/2016 | Pagès et al. |
| 9,393,359 B2 | 7/2016 | Boggs et al. |
| 10,758,652 B2 | 9/2020 | Ragusa |
| 10,946,131 B2 | 3/2021 | Patel et al. |
| 10,980,934 B2 | 4/2021 | Ragusa |
| 11,110,216 B2 | 9/2021 | Patel et al. |
| 11,412,967 B2 * | 8/2022 | Patel ............... A61M 1/265 |
| 11,801,001 B2 * | 10/2023 | Patel ............... A61M 1/385 |
| 2001/0000018 A1 | 3/2001 | Truong et al. |
| 2001/0027156 A1 | 10/2001 | Egozy et al. |
| 2002/0043492 A1 | 4/2002 | Bischof |
| 2002/0062100 A1 | 5/2002 | Pierce et al. |
| 2002/0120227 A1 | 8/2002 | Childers et al. |
| 2002/0151804 A1 | 10/2002 | O'mahony et al. |
| 2003/0055375 A1 | 3/2003 | Holst et al. |
| 2003/0066807 A1 | 4/2003 | Suzuki |
| 2003/0125017 A1 | 7/2003 | Greene et al. |
| 2003/0125881 A1 * | 7/2003 | Ryan ............... A61M 1/3496 702/45 |
| 2003/0140928 A1 | 7/2003 | Bui et al. |
| 2003/0175150 A1 | 9/2003 | Grimm |
| 2004/0183683 A1 | 9/2004 | Funahashi |
| 2004/0186409 A1 | 9/2004 | Cavalcanti et al. |
| 2004/0199098 A1 | 10/2004 | Pierce et al. |
| 2005/0131334 A1 | 6/2005 | Langley et al. |
| 2005/0209522 A1 | 9/2005 | Tadokoro et al. |
| 2005/0228238 A1 | 10/2005 | Monitzer |
| 2005/0235733 A1 | 10/2005 | Holst et al. |
| 2005/0258238 A1 | 11/2005 | Chapman |
| 2006/0058167 A1 | 3/2006 | Ragusa et al. |
| 2006/0093190 A1 | 5/2006 | Cheng et al. |
| 2006/0155236 A1 | 7/2006 | Gara et al. |
| 2006/0226086 A1 | 10/2006 | Robinson et al. |
| 2007/0018832 A1 | 1/2007 | Beigel et al. |
| 2007/0067452 A1 | 3/2007 | Fung et al. |
| 2007/0112289 A1 | 5/2007 | Cavalcanti et al. |
| 2007/0138069 A1 | 6/2007 | Roncadi et al. |
| 2007/0258626 A1 | 11/2007 | Reiner |
| 2007/0268130 A1 | 11/2007 | Yee et al. |
| 2008/0146993 A1 | 6/2008 | Krishna |
| 2009/0215602 A1 | 8/2009 | Min et al. |
| 2009/0275808 A1 | 11/2009 | Dimaio et al. |
| 2010/0100392 A1 | 4/2010 | Rothman et al. |
| 2012/0010062 A1 | 1/2012 | Fletcher et al. |
| 2012/0053501 A1 | 3/2012 | Brown et al. |
| 2012/0175313 A1 | 7/2012 | Barry, Jr. et al. |
| 2013/0081998 A1 | 4/2013 | Chamney et al. |
| 2013/0267884 A1 | 10/2013 | Boggs et al. |
| 2014/0039373 A1 | 2/2014 | Ragusa et al. |
| 2014/0356851 A1 | 12/2014 | Pagès et al. |
| 2015/0367063 A1 | 12/2015 | Kimura |
| 2017/0239409 A1 | 8/2017 | De los Reyes, et al. |
| 2018/0052978 A1 | 2/2018 | Benjamin et al. |
| 2018/0344910 A1 | 12/2018 | Ragusa |
| 2018/0344921 A1 * | 12/2018 | Ragusa ............... A61M 1/385 |
| 2020/0345924 A1 | 11/2020 | Ragusa |
| 2021/0015989 A1 | 1/2021 | Patel et al. |

FOREIGN PATENT DOCUMENTS

| | | |
|---|---|---|
| CN | 102395392 A | 3/2012 |
| CN | 104800905 A | 7/2015 |
| CN | 204446748 U | 7/2015 |
| CN | 112105403 A | 12/2018 |
| EP | 0128683 A2 | 12/1984 |
| EP | 0171749 A1 | 2/1986 |
| EP | 0208061 A1 | 1/1987 |
| EP | 0229504 A2 | 7/1987 |
| EP | 0257755 A1 | 3/1988 |
| EP | 0350162 A1 | 1/1990 |
| EP | 0578086 A1 | 1/1994 |
| EP | 0619145 A2 | 10/1994 |
| EP | 0654277 A1 | 5/1995 |
| EP | 0664159 A1 | 7/1995 |
| EP | 0799645 A1 | 10/1997 |
| EP | 0885619 A1 | 12/1998 |
| EP | 1057534 A1 | 12/2000 |
| EP | 1295619 A2 | 3/2003 |
| EP | 1374927 A1 | 1/2004 |
| EP | 2650030 A1 | 10/2013 |
| FR | 2258898 A1 | 10/1977 |
| GB | 2017110 A | 10/1979 |
| JP | S596952 A | 1/1984 |
| JP | S5969166 A | 4/1984 |
| JP | H0252665 A | 2/1990 |
| JP | H03131268 A | 6/1991 |
| JP | H0775746 A | 3/1995 |
| JP | H08131539 A | 5/1996 |
| JP | H09192215 A | 7/1997 |
| JP | 2002282352 A | 10/2002 |
| JP | 2002291872 A | 10/2002 |

(56) References Cited

FOREIGN PATENT DOCUMENTS

| | | |
|---|---|---|
| JP | 2003525709 A | 9/2003 |
| JP | 3936132 B | 6/2007 |
| JP | 2008506424 A | 3/2008 |
| JP | 2008194067 A | 8/2008 |
| JP | 2014041600 | 3/2014 |
| RU | 2252788 C1 | 5/2005 |
| SU | 660718 A1 | 5/1979 |
| SU | 762982 A1 | 9/1980 |
| SU | 1146098 A1 | 3/1985 |
| WO | 8502561 A1 | 6/1985 |
| WO | 9000059 A1 | 1/1990 |
| WO | 9007383 A1 | 7/1990 |
| WO | 9406535 A1 | 3/1994 |
| WO | 9611747 A2 | 4/1996 |
| WO | 9633023 A1 | 10/1996 |
| WO | 0205059 A2 | 1/2002 |
| WO | 2007041716 A1 | 4/2007 |
| WO | 2018222441 A1 | 12/2018 |
| WO | 2019084278 A1 | 5/2019 |
| WO | 2019226654 A1 | 11/2019 |

OTHER PUBLICATIONS

Vassallo, R.R. et al., Improved donor safety in high-volume apheresis collections, Transfusion Feb. 1, 2017 Blackwell Publishing Inc., USA, vol. 57, pp. 319-324, Feb. 2017.
Vurro, F. et al., Quantitative assessment of the anticoagulant in plasma units collected by plasmapheresis, Transfusion (Malden), vol. 59, pp. 2113-2120, Jun. 2019.
Way, B. et al., Inova blood donor center experience with Trima Accel 7, Transfusion Sep. 1, 2019 Blackwell Publishing Inc., vol. 59, pp. 48A-49A, Sep. 2019.
Way, B. et al., Inova blood donor center experience with Trima Accel 7, Transfusion Sep. 9, 2019 Blackwell Publishing Inc., vol. 59, p. 48A-49A, Sep. 2019.
Williams, A.E., FDA Considerations Regarding Frequent Plasma Collection Procedures, www.ihn-org.com, 2013.
Winters, J.L. et al., American Society for Apheresis guidelines on the use of apheresis in clinical practice: practical, concise, evidence-based recommendations for the apheresis practitioner, Journal of clinical apheresis, United States, vol. 29, pp. 191-193, Aug. 2014.
Altunatas, F., et al., Comparison of Plateletpheresis on the Fenwal Amicus and Fresenius Com. Tec Cell Separators, Transfusion Medicine and Hemotherapy, vol. 35, pp. 368-373, 2008.
Amendment and Argument filed on Aug. 6, 2021 in Korean Application No. 10-2020-7033247 with English translation (11 pages.).
Amendment and Argument filed on Dec. 15, 2021 in Japanese Application No. 2020202093 with English translation (12 pages.).
Amendment and Reply in U.S. Appl. No. 16/739,441 dated Apr. 5, 2022, 13 pages.
Amendment filed in U.S. Appl. No. 17/306,099, dated Nov. 2, 2021, 17 pages.
Amendment in U.S. Appl. No. 17/306,099 dated Apr. 5, 2022, 18 pages.
Amendment to the application with English translation for Korean Patent Application No. 10-2020-7033175 dated May 24, 2021 (11 pages).
Amendment to the application with English translation for Korean Patent Application No. 10-2020-7033247 dated May 24, 2021 (40 pages).
Anonymous, 21 CFR Parts 606, 610, 630, et 1.; Requirements for Blood and Blood Components Intended for Transfusion or for Further Manufacturing Use; Final Rule, Federal Register. vol. 80, 2015.
Anonymous, Code of Federal Regulations, §606.110 General donor eligibility requirements, Code of Federal Regulations, National Archives, May 2020.
Anonymous, Code of Federal Regulations, §630.10 General donor eligibility requirements, Code of Federal Regulations, National Archives, May 2020.
Anonymous, Code of Federal Regulations, §630.15 Donor eligibility requirements, Code of Federal Regulations, National Archives, May 2020.
Anonymous, Code of Federal Regulations, §640.65 Plasmapheresis, Code of Federal Regulations, National Archives, pp. 105-107, Apr. 2020.
Applicant-Initiated Interview Summary, U.S. Appl. No. 17/306,099, dated Nov. 5, 2021, 17 pages.
Bialkowski W., et al., Citrate anticoagulation: Are blood donors donating bone?, Journal of clinical apheresis, United States, vol. 31, pp. 459-463, Oct. 2016.
Blaha, M. et al., Experience with extracorporeal elimination therapy in myasthenia gravis, Transfusion and Apheresis Science Elsevier Science, London, GB, vol. 45, pp. 252-256, 2011.
Burgstaler, E. A., Blood component collection by apheresis, Journal of clinical apheresis, United States, Journal of clinical apheresis, United States, vol. 21, pp. 142-151, Jul. 2006.
Burgstaler, E.A., et al., Paired comparison of therapeutic plasma exchange using the Fenwal Amicus versus TerumoBCT Spectra Optia, Journal of clinical apheresis, United States, vol. 33, pp. 265-273, Jun. 2018.
Canadian Requisition by the Examiner in Accordance with Subsection 86(2) of the Patent Rules Dated Sep. 28., 2021 for Canadian Application No. 3,099,428.
Caridian BCT; Operator's Manual: Trims Accel® Automated Blood Collection System for Version 6.0 with Automated RBC Processes; Part No. 777095-197, Jun. 2010, (296 pages).
Charifa, A. et al., Transfusion medicine equations made internet accessible, American Journal of Clinical Pathology Oct. 10, 2018, Oxford University Press, vol. 150, Oct. 2018.
China National Intellectual Property Administration Notification of the First Office Action dated Dec. 6, 2021 for Chinese International Application No. 201980031598.1.
Colpo, A., et al., Therapeutic apheresis during pregnancy: A single center experience, Transfusion And Apheresis Science, Elsevier Science, London, GB, Sep. 5, 2019.
Communication pursuant to Article 94(3) EPC, App. No. 21198088.3, dated Jun. 13, 2022, 6 pages.
Compliance Program Guidance Manual, Chapter 42-Blood and Blood Components, Inspection of Source Plasma Establishments, Brokers, Testing Laboratories, and Contractors-7342.002, Completion Date: Jan. 31, 2019, (63 pages).
Cordts, P.R. et al., Poor predictive value of hematocrit and hemodynamic parameters for erythrocyte deficits after extensive elective vascular operations, Surgery, gynecology & obstetrics, United States, vol. 175, pp. 243-248, Sep. 1992.
De Back, D. Z. et al., Therapeutic plasma apheresis: Expertise and indications, Transfusion and Apheresis Science, vol. 58, pp. 254-257, Jun. 2019.
Director, Center for Biologics Evaluation and Research, Volume Limits for Automated Collection of Source Plasma, Nov. 4, 1992 (3 pages).
Evers, D. et al., The efficiency of therapeutic erythrocytapheresis compared to phlebotomy: a mathematical tool for predicting response in hereditary hemochromatosis, polycythemia vera, and secondary erythrocytosis, Journal of clinical apheresis, United States, vol. 29, pp. 133-138, Jun. 2014.
Evers, J. et al., Distribution of citrate and citrate infusion rate during donor plasmaphereses, Journal of clinical apheresis, United States, vol. 31, pp. 59-62, Feb. 2016.
Examination report No. 1 for standard patent application for Australian patent No. 2019274489 dated Nov. 16, 2020 (4 pages).
Examination report No. 1 for standard patent application for Australian patent No. 2020267188 dated Nov. 25, 2020 (7 pages).
Examiner Requisition in Canada App. 3,099,428 dated Mar. 28, 2022, 4 pages.
Extended European Search Report dated Nov. 8, 2021 for European Application No. 21183088.0.
Extended European Search Report, counterpart EP Application No. 21168049.1 (dated Aug. 17, 2021) (8 pages).
Feldschuh, J. et al., Prediction of the Normal Blood Volume Relation of Blood Volume To Body Habitus, Circulation 1977, vol. 56, pp. 605-612, Oct. 1977.

(56) References Cited

OTHER PUBLICATIONS

Feldschuh, J. et al., The importance of correct norms in blood volume measurement, The American journal of the medical sciences, United States, vol. 334, pp. 41-46, Jul. 2007.
Fenwal: AMICUSTM Separator: Operator's Manual SW v. 4.3; REF 4R4580, 4R4580R, Jun. 2011, (501 pages).
Fenwal: AMICUSTM Separator: Therapeutics Supplement Manual SW v. 4.2, Mononuclear Cell Collection + Therapeutic Plasma Exchange; REF 4R4580, 4R4580R, Apr. 2011, (372 pages).
Fenwal: AMICUSTM Separator: Therapeutics Supplement Manual SW v. 4.3, Mononuclear Cell Collection + Therapeutic Plasma Exchange; REF 4R4580, 4R4580R, Mar. 2012, 372 pages.
Fresenius Kabi: AMICUS Separator: Operator's Manual SW v. 5.1, vol. 2—Platelets with Concurrent Plasma or RBC Collection, REF 4R4580, 4R4580R, 4R4580TH, 6R4580, 6R4580R, Mar. 2017, 352 pages.
Fresenius Kabi: AMICUS Separator: Operator's Manual SW v. 5.1, vol. 2—Platelets with Concurrent Plasma or RBC Collection, REF 4R4580, 4R4580R, 4R4580TH, 6R4580, 6R4560R, Mar. 2017, 352 pages.
Gokay, S. et al., Long-term efficacy of lipoprotein apheresis in the management of familial hypercholesterolaemia: Application of two different apheresis techniques in childhood, Transfusion and Apheresis Science, Elsevier Science, London, GB, vol. 54, pp. 282-288, Nov. 2, 2012.
Hadem, J. et al., Therapeutic plasma exchange as rescue therapy in severe sepsis and septic shock: retrospective observational single-centre study of 23 patients, BMC Anesthesiology, Biomed Central, London, GB, vol. 14, p. 24, Apr. 2014.
Hafer, C. et al., Membrane versus centrifuge-based therapeutic plasma exchange: a randomized prospective crossover study, International urology and Nephrology, Akademiai, Budapest, HU, vol. 48, pp. 133-138, Nov. 3, 2015.
Hafer, C. et al., Pro: High dose of therapeutic plasma exchange—mind the gap!, Nephrology, dialysis, transplantation official publication of the European Dialysis and Transplant Association—European Renal Association England; vol. 32, pp. 1457-1460, Sep. 1, 2017.
Hattersley, J.G. et al., Describing the effectiveness of immunosuppression drugs and apheresis in the treatment of transplant patients, Computer Methods and Programs in Biomedicine, Amsterdam, NL, vol. 109, pp. 126-133, Feb. 10, 2012.
Hauser, R. G. et al., Transfusion Medicine Equations Made Internet Accessible, Transfusion Medicine Reviews, Nov. 16, 2019 Grune and Stratton, Orlando, FL, US, vol. 34, Nov. 2019.
International Search Report and Written Opinion dated Dec. 1, 2021 for International Application No. PCT/US2021/047124.
Notice of Reasons for Refusal in JP Pat App 2022-104191, Dec. 14, 2023, 12 pages.
Notice of Reasons for Refusal in JP Pat App 2023-544359, Nov. 30, 2023, 11 pages.
China App. No. 202180091469.9, Feb. 29, 2024, Notification of the First Office Action, Text of the First Office Action, Search Report, 7 pages.
International Search Report and Written Opinion dated Sep. 30, 2021 for International Application No. PCT/JS21/33835.
International Search Report and Written Opinion for Application No. PCT/US2018/033826, dated Aug. 3, 2018, 10 pages.
International Search Report and Written Opinion for Application No. PCT/US2018/57528, dated Jan. 7, 2019, 17 pages.
International Search Report and Written Opinion, counterpart International App. No. PCT/US2021/033835 (dated Sep. 30, 2021) (20 pages).
International Search Report and Written Opinion, counterpart International Appl. No. PCT/US2019/033318 (dated Aug. 21, 2019) (14 pages).
Jia, Z.S. et al., Total blood volume of Asian patients undergoing cardiac surgery is far from that predicted by conventional methods, The Journal of cardiovascular surgery, Italy, vol. 54, pp. 423-430, Jun. 2013.
Kawai, Y. et al., Therapeutic plasma exchange may improve hemodynamics and organ failure among children with sepsis-induced multiple organ dysfunction syndrome receiving extracorporeal life support, Pediatric critical care medicine: a journal of the Society of Critical Care Medicine and the World Federation of Pediatric Intensive and Critical Care Societies, United States, vol. 16, pp. 366-374, May 2015.
Keklik, M. et al., Effectiveness of the haemonetics MCS cell separator in the collection of apheresis platelets, Transfusion and Apheresis Science Elsevier Science, London, GB, vol. 53, pp. 396-398, Aug. 2015.
Kochinke, F. et al., Modelling of LDL-apheresis: System efficacy and rebound kinetics, Plasma Therapy and Transfusion Technology, vol. 9, pp. 35-44, 1988.
Kuan, Jew-Win et al., A randomized double blind control trial comparing filgrastim and pegfilgrastim in cyclophosphamide peripheral blood hematopoietic stem cell mobilization, Transfusion and Apheresis Science Elsevier Science, London, GB, vol. 53, pp. 196-204, Mar. 2015.
Kube{hacek over (c)}ek, O. et al., Plasmafiltration as an effective method in the removal of circulating pegylated liposomal doxorubicin (PLD) and the reduction of mucocutaneous toxicity during the treatment of advanced platinum-resistant ovarian cancer, Cancer Chemotherapy and Pharmacology, Springer Verlag, Berlin, DE, vol. 85, pp. 353-365, Nov. 14, 2019.
Lambert, C. et al., Plasma extraction rate and collection efficiency during therapeutic plasma exchange with Spectra Optia in comparison with Haemonetics MCS+, Journal of clinical apheresis, United States, vol. 26, pp. 17-22, 2011.
Lemmens, H. et al., Estimating Blood Volume in Obese and Morbidly Obese Patients, Obesity Surgery, vol. 16, pp. 773-776, 2006.
Lin, Shi-Woei et al., Optimal collecting policy for apheresis platelets in a regional blood center, Vox Sanguinis, vol. 115, Feb. 2020.
Linderkamp, O. et al., Estimation and Prediction of Blood Volume in Infants and Children, European Journal of Pediatrics, vol. 125, pp. 227-234, Aug. 1977.
Lopez, A.J., et al., Monitoring and isolation of blood dendritic cells from apheresis products in healthy individuals: a platform for cancer immunotherapy, Journal of Immunological Methods, Sep. 15, 2002 Elsevier Science Publishers B. V., Amsterdam, NL, vol. 267, pp. 199-212, Sep. 2002.
Lopez, A.J., et al., Monitoring and isolation of blood dendritic cells from apheresis products in healthy individuals: a platform for cancer immunotherapy, Journal of Immunological Methods, Sep. 9, 2002 Elsevier Science Publishers B.V., Amsterdam, NL, vol. 267, pp. 199-212, Sep. 2002.
Maitta, Robert W., Current state of apheresis technology and its applications, Transfusion and Apheresis Science, vol. 57, pp. 606-613, Oct. 2018.
Merolle, L., et al., The effect of donor's characteristics on plasmapheresis products: insights for a personalised approach Blood transfusion = Trasfusione del sangue, Italy, May 2020.
Miladi, M.I. et al., Relevance of plasma exchange in the treatment of myasthenia gravis: Study of 11 cases, Revue de Medecine Interne Feb. 2008, France, vol. 29, pp. 87-93.
Milan, B. et al., Experience with extracorporeal elimination therapy in myasthenia gravis, Transfusion and Apheresis Science Elsevier Science, London, GB, vol. 45, pp. 252-256, 2011.
Neff, L.P., The use of theraputic plasma exchange (TPE) in the setting of refractory burn shock, Burns 2010 Elsevier Ltd., vol. 36, pp. 372-378, 2010.
Neyrinck, M.M et al., Calculations in apheresis, Journal of clinical apheresis, vol. 30, pp. 38-42, Feb. 2015.
Notice for Reasons for Refusal in Japan App. 2020-202093 dated Jan. 11, 2022, 3 pages.
Notice of Allowance in U.S. Appl. No. 17/386,992 dated Feb. 9, 2022, 8 pages.
Notice of Preliminary Rejection with English translation for Korean Patent Application No. 10-2020-7033247 dated Mar. 22, 2021 (31 pages).
Notice of Reasons of Refusal with English translation, counterpart Japanese application 2020-202093 dated Jun. 15, 2021 (8 pages).

(56) References Cited

OTHER PUBLICATIONS

Notice of Reasons of Refusal with English translation, counterpart Japanese application 2020-557304 dated May 11, 2021 (8 pages).
Office communication in U.S. Appl. No. 17/078,824 dated Nov. 3, 2021, 22 pages.
Office communication in U.S. Appl. No. 17/306,099 dated Dec. 6, 2021, 17 pages.
Office communication in U.S. Appl. No. 17/306,099 dated Sep. 23, 2021, 19 pages.
Pearson, T.C. et al., Interpretation of measured red cell mass and plasma volume in adults: Expert Panel on Radionuclides of the International Council for Standardization in Haematolog, British journal of haematology, England, vol. 89, pp. 748-756, Apr. 1995.
Perry, F.A. et al., Blood volume replacement in surgical patients; Surgical Clinics of North America, pp. 301-313, Apr. 1956.
Pratx, L.B. et al., Development of apheresis techniques and equipment designed for patients weighing less than 10 kg, Transfusion and Apheresis Science, vol. 57, pp. 331-336, Jun. 2018.
Request for Examination in EP21168049 dated Mar. 29, 2022, 12 pages.
Response to Examiner's Report for Australian Patent Application 2019274489 dated Mar. 16, 2021 (12 pages) (12 pages).
Response to Examiner's Report for Australian Patent Application 2020267188 dated Mar. 16, 2021 (12 pages) (20 pages).
Response to Non-Final Office Action in U.S. Appl. No. 17/078,824 dated Apr. 4, 2022, 11 pages.
Response to Notice of Preliminary Rejection with English translation for Korean Patent Application No. 10-2020-7033175 dated May 24, 2021 (33 pages).
Response to Notice of Preliminary Rejection with English translation for Korean Patent Application No. 10-2020-7033247 dated May 24, 2021 (42 pages).
Russian Patent Office, Russian Search Report for RU2252788C1 with English translation dated Jun. 2, 2021 (4 pages).
Schettler, V. et al., How to optimize lipoprotein apheresis treatment-A second look, Atherosclerosis Supplements, vol. 14, pp. 89-92, Jan. 2013.
Schwartz, J. et al., Guidelines on the Use of Therapeutic Apheresis in Clinical Practice-Evidence-Based Approach from the Writing Committee of the American Society for Apheresis: The Seventh Special Issue, Journal of clinical apheresis, United States, vol. 31, pp. 149-162, Jun. 2016.
Setia, R.D. et al., Comparison ofAmicus and COBE Spectrafor allogenic peripheral blood stem cell harvest: Study from tertiary care centre in India, Transfusion And Apheresis Science, Elsevier Science, London, GB, vol. 56, pp. 439-444, Apr. 24, 2017.
Simsir, I.Y. et al., Therapeutic plasmapheresis in thyrotoxic patients, Endocrine, Humana Press, Inc, US, vol. 62, pp. 144-148, Jul. 2, 2018.
Sprenger, K.B., Nomograms for the prediction of patients plasma vol. in plasma exchange therapy from height, weight, and hematocrit, Journal of clinical apheresis, United States, vol. 3, pp. 185-190, Jan. 1987.
Staley, E. M. et al., A brief review of common mathematical calculations in therapeutic apheresis, Journal of clinical apheresis, United States, vol. 34, pp. 607-612, Oct. 2019.
Technical Manual 20th edition, Methods and Appendices, http://www.aabb.org/programs/publications/Pages/tech-manual-methods.aspx, 2020.
Trima Accel Automated Blood Collection System Service Manual, pp. 1-340 (2015).
Valbonesi, A.M. et al., Plateletpheresis: What's new?, Transfusion Science, Dec. 1, 1996 Pergamon Press, Oxford, GB, vol. 17, pp. 537-544, Dec. 1996.
Communication in EP Application No. EP21921581.1, dated Apr. 22, 2024, 7 pages.
The Second Office Action in China App. No. 202180071948.4, dated Jun. 29, 2024, 4 pages.
Decision of Refusal, Japan Patent App. No. 2023-544359 dated Jun. 6, 2024, 4 pages.

\* cited by examiner

VOLUME OF RAW PLASMA IN PLASMA PRODUCT (mL) FOR A 1:16 AC RATIO

| DONOR WEIGHT LBS | PLASMA PRODUCT VOLUME (mL) | DONOR HEMATOCRIT (%) | | | | | | | | | | |
|---|---|---|---|---|---|---|---|---|---|---|---|---|
| | | 36 | 38 | 40 | 42 | 44 | 46 | 48 | 50 | 52 | 54 | 56 |
| 110-149 | 690 | 629 | 627 | 625 | 623 | 621 | 618 | 616 | 613 | 611 | 607 | 604 |
| 150-174 | 825 | 752 | 749 | 747 | 745 | 742 | 739 | 736 | 733 | 730 | 726 | 722 |
| 175 & up | 880 | 802 | 799 | 797 | 794 | 792 | 789 | 786 | 782 | 779 | 775 | 771 |

Fig. 7

UNCLAIMED RAW PLASMA (mL) FOR A 1:16 AC RATIO

| DONOR WEIGHT LBS | PLASMA PRODUCT VOLUME (mL) | DONOR HEMATOCRIT (%) | | | | | | | | | | |
|---|---|---|---|---|---|---|---|---|---|---|---|---|
| | | 36 | 38 | 40 | 42 | 44 | 46 | 48 | 50 | 52 | 54 | 56 |
| 110-149 | 690 | -4 | -2 | 0 | 2 | 4 | 7 | 9 | 12 | 14 | 18 | 21 |
| 150-174 | 825 | -2 | 1 | 3 | 5 | 8 | 11 | 14 | 17 | 20 | 24 | 28 |
| 175 & up | 880 | -2 | 1 | 3 | 6 | 8 | 11 | 14 | 18 | 21 | 25 | 29 |

Fig. 8

ALLOWED PLASMA PRODUCT VOLUME (mL) FOR A 1:16 AC RATIO

| DONOR WEIGHT LBS | DONOR HEMATOCRIT (%) | | | | | | | | | | | |
|---|---|---|---|---|---|---|---|---|---|---|---|---|
| | RAW VOLUME | 36 | 38 | 40 | 42 | 44 | 46 | 48 | 50 | 52 | 54 | 56 |
| 110-149 | 625 | 686 | 688 | 690 | 692 | 695 | 697 | 700 | 703 | 706 | 710 | 714 |
| 150-174 | 750 | 823 | 826 | 828 | 831 | 834 | 837 | 840 | 844 | 848 | 852 | 857 |
| 175 & up | 800 | 878 | 881 | 883 | 886 | 889 | 893 | 896 | 900 | 904 | 909 | 914 |

Fig. 9

| INPUTS | |
|---|---|
| DONOR WEIGHT (lbs) | 190 |
| STARTING DONOR HCT (%) | 44 |
| TARGET RAW PLASMA VOL (mL) | 800 |
| BLOOD VOLUME (mL/kg) | 62.5 |
| PLASMA REPLACEMENT RATE (mL/min) | 0 |
| DONOR WEIGHT (kg) | 86.4 |
| RBC VOLUME (mL) | 2375 |
| PLASMA VOLUME (mL) | 3023 |
| DRAW VOLUME (mL WB) | 500 |
| AC RATIO (1:xx) | 16 |
| EFFICIENCY | 70% |

*Fig. 10*

| DESCRIPTION | DONOR RBC VOL (mL) | DONOR PLASMA VOL (mL) | DONOR HCT (%) | AC DRAWN (mL) | RBC DRAWN (mL) | RAW PLASMA DRAWN (mL) |
|---|---|---|---|---|---|---|
| CYCLE 1 START | 2375 | 3023 | 44.0% | | | |
| CYCLE 1 DRAW END | 2155 | 2743 | 44.0% | 31 | 220 | 280 |
| CYCLE 1 RETURN END | 2375 | 2836 | 45.6% | | | |
| CYCLE 2 DRAW END | 2147 | 2564 | 45.6% | 31 | 228 | 272 |
| CYCLE 2 RETURN END | 2375 | 2655 | 47.2% | | | |
| CYCLE 3 DRAW END | 2139 | 2391 | 47.2% | 31 | 236 | 264 |
| CYCLE 3 RETURN END | 2375 | 2480 | 48.9% | | | |
| CYCLE 4 DRAW END | 2130 | 2224 | 48.9% | 31 | 245 | 255 |
| CYCLE 4 RETURN END | 2375 | 2310 | 50.7% | | | |
| CYCLE 5 DRAW END | 2301 | 2239 | 50.7% | 31 | 245 | 255 |
| CYCLE 5 RETURN END | 2375 | 2263 | 51.2% | | | |

*Fig. 11a*

| DESCRIPTION | RESERVOIR RBC VOL (mL) | RESERVOIR NON RBC VOL (mL) | COLLECTION VOL (mL) | COLLECTED PLASMA (mL) | COLLECTED RAW VOL (mL) | TARGET COLLECTION VOL (mL) |
|---|---|---|---|---|---|---|
| CYCLE 1 START | 0 | 0 | 0 | 0 | | 889 |
| CYCLE 1 DRAW END | 220 | 93 | 218 | 196 | | |
| CYCLE 1 RETURN END | 0 | 0 | 218 | 196 | | 891 |
| CYCLE 2 DRAW END | 228 | 91 | 430 | 386 | | |
| CYCLE 2 RETURN END | 0 | 0 | 430 | 386 | | 893 |
| CYCLE 3 DRAW END | 236 | 89 | 637 | 571 | | |
| CYCLE 3 RETURN END | 0 | 0 | 637 | 571 | | 894 |
| CYCLE 4 DRAW END | 245 | 86 | 837 | 750 | | |
| CYCLE 4 RETURN END | 0 | 0 | 837 | 750 | | 894 |
| CYCLE 5 DRAW END | 74 | 24 | 894 | 800 | | |
| CYCLE 5 RETURN END | 0 | 0 | 894 | 800 | | 894 |

*Fig. 11b*

SYSTEMS AND METHODS FOR PLASMA COLLECTION

CROSS-REFERENCE TO RELATED APPLICATIONS

The present application is a Continuation of U.S. Ser. No. 17/861,437, filed Jul. 11, 2022, which is a Continuation of U.S. Ser. No. 17/306,099, filed May 3, 2021, which claims the benefit of U.S. 63/140,534, filed Jan. 22, 2021 and which is a Continuation-in Part of U.S. Ser. No. 16/739,441, filed Jan. 10, 2020; which is a Continuation of PCT/US2019/033318, filed May 21, 2019, which claims the benefit of each of U.S. 62/846,400, filed May 10, 2019, U.S. 62/752,480, filed Oct. 30, 2018, and U.S. 62/674,144, filed May 21, 2018, all of the above applications being incorporated by reference herein in their entireties.

BACKGROUND

The present application relates to systems and methods for performing plasmapheresis and, more particularly, to plasmapheresis systems and methods in which the volume of pure plasma that may be collected from a particular donor is optimized.

Plasmapheresis is an apheresis procedure in which whole blood is withdrawn from a donor, plasma is separated from other cellular blood components (red blood cells, platelets, and leukocytes) and retained, and the cellular blood components are returned to the donor. The separation of the plasma from the cellular components is typically accomplished in an automated procedure by centrifugation or membrane filtration.

In automated plasmapheresis, whole blood is drawn from the donor, mixed at a specified ratio with anticoagulant, and then separated into plasma, red blood cells, and other cellular components. Once a target volume of anticoagulated plasma (or "plasma product") has been collected, as determined by a weigh scale associated with a plasma collection container, the withdrawal of whole blood from the donor ceases, and the red blood cells and other cellular components are returned to the donor. Often, the plasma product is collected in multiple collection and reinfusion cycles, until the total target volume of anticoagulated plasma has been collected. The anticoagulated plasma may be used for later transfusion or further manufacturing.

Plasma that is collected to serve as a source material ("source plasma") for further manufacturing is collected from multiple donors and combined or pooled together for this purpose. The FDA issued guidelines for registered blood collection centers as to the volume of plasma that may be collected as source plasma during plasmapheresis in order to improve the consistency of procedures for manufacturing source plasma, and to minimize the opportunity for staff error. (FDA Memo: "Volume Limits-Automated Collection of Source Plasma (11/4/92)").

The FDA Memo set forth a simplified plasma volume nomogram, in which the volume (or weight) of pure (or raw) plasma that may be collected from a particular donor is limited to ensure donor safety and comfort. More specifically, the FDA nomogram limits the volume (or weight) of plasma based on the weight of the donor, and establishes the volume of anticoagulant that may be added to a 1:16 ratio of anticoagulant to anticoagulated blood, or 0.06 parts anticoagulant to 1 part anticoagulated blood, to arrive at a maximum collection volume for the total of the plasma plus the anticoagulant for a particular donor.

The simplified nomogram set forth in the FDA Memo has been the predominant method for determining plasma product collection volumes used by blood collection centers. Therefore, the plasmapheresis devices used at such centers are commonly programmed to collect a specified volume/weight of anticoagulated plasma (assuming a known density) in accordance with the maximum collection volume permitted by the FDA nomogram, with the anticoagulant being added to the whole blood at a 1:16 or 0.06 ratio.

One simplification made in the FDA nomogram is to exclude the consideration of donor hematocrit in determining the targeted collection volume for the plasma product. However, the relative proportions of pure plasma and anticoagulant in the plasma product depends on the donor blood hematocrit and the ratio at which the anticoagulant is combined with the donor's whole blood. As a consequence, higher hematocrit donors reach the maximum collection volume set forth in the FDA nomogram before reaching the maximum pure plasma volume that may be safely collected from the donor. This represents an inefficiency for the plasma collection center, in that the volume of pure plasma that is collected is less than the maximum amount possible.

Further, the amount of pure plasma that may be safely collected from a donor can depend on factors in addition to the donor's weight and hematocrit that affect the donor's total blood volume, such as the donor's height.

Because the source plasma from multiple donors is combined, it is important to maximize the pure plasma volume that may be collected from each individual donor, as even small gains in volume collected from each individual donor, when added together, result in a meaningful increase in the total volume of the pooled plasma. If a plasmapheresis device were to be able to better target the pure plasma volume, more plasma proteins could be collected from each donor, improving the overall efficiency of the plasma collection center. Accordingly, by way of the present disclosure, systems and methods for optimizing the volume of plasma collected are provided which are consistent with donor safety and comfort.

SUMMARY

In a first aspect of the present disclosure, a system is provided for collecting plasma from a donor in which the system comprises: a venipuncture needle for withdrawing whole blood from the donor, a blood separator for separating the whole blood into a plasma product and a second blood component comprising red blood cells, a donor line coupled to the venipuncture needle for introducing whole blood from the donor to the blood separator, a first pump for controlling flow through the donor line, an anticoagulant line coupled to an anticoagulant source for combining anticoagulant with the whole blood, and a second pump for controlling flow through the anticoagulant line.

A touchscreen is provided for receiving input from an operator to a controller programmed to control operation of the system. The controller is configured to determine a target volume of plasma product to be collected (TVPP), either based on the weight of the donor and the donor hematocrit, or based on the weight and height of the donor and the donor hematocrit, to control the system to operate a draw and return cycle to withdraw whole blood from the donor, to add anticoagulant to the whole blood at a pre-determined ratio (ACR), to separate the anticoagulated whole blood into the plasma product and the second component and to return the second component to the donor, and to stop withdrawing whole blood from the donor and initiate a final return of the second blood component when a measured volume of plasma product in a plasma collection container reaches the target volume for plasma product.

In a second aspect, the controller is programmed to calculate i) a target volume of pure plasma to be collected (TVP) based on the weight of the donor and ii) a percentage of anticoagulant in the target volume of plasma product to be collected (% $AC_{TVPP}$) based on the pre-determined anticoagulant ratio, ACR, and the donor hematocrit, wherein the TVPP=TVP/(1−% $AC_{TVPP}$).

In a third aspect, the controller is programmed to calculate a total blood volume of the donor (TBV) based on the weight and height of the donor, a target volume of pure plasma to be collected (TVP) as a percentage of the TBV, and a percentage of anticoagulant in the target volume of plasma product to be collected (% $AC_{TVPP}$) based on the pre-determined anticoagulant ratio (ACR) and the donor hematocrit, wherein the TVPP=TVP/(1−% $AC_{TVPP}$).

In a fourth aspect, the controller is programmed to calculate the total blood volume of the donor (TBV) based on the weight and height of the donor to calculate a body mass index for the donor (BMI) such that TBV=70/(sqrtBMI/22) (Lemmens equation).

In a fifth aspect, the controller is programmed to calculate the total blood volume of the donor (TBV) based on the weight (Wt), height (Ht) and sex (Male or Female) of the donor such that TBV=(0.3669*$Ht^3$)+(0.03219*Wt)+0.6041 for Males and TBV=(0.3561*$Ht^3$)+(0.03308*Wt)+0.1833 for Females, where Ht is in meters and Wt is in kilograms (Nadler's formula).

In a sixth aspect, methods are provided for performing plasmapheresis to collect a volume of plasma product (i.e., anticoagulated plasma, VPP) so that that the targeted volume of pure plasma (TVP) in the plasma product is determined based on donor-specific characteristics, consistent with the donor's safety and comfort. In particular, the targeted volume of pure plasma to be collected, TVP, is based on the weight, or the weight and the height, of the donor.

In a seventh aspect, the targeted volume of pure plasma to be collected, TVP, may be a multiple of the donor's weight. Alternatively, TVP may be a multiple of the donor's total blood volume, TBV, with the TBV of the donor being determined based on the donor's weight and height, using well established methodology, such as the Lemmens equation or Nadler's formula.

A target volume for the plasma product to be collected, TVPP, is established based on the target volume/weight of pure plasma and the percentage of anticoagulant, AC, in the plasma product, % $AC_{TVPP}$, such that TVPP=TVP/(1−% $AC_{TVPP}$), wherein % $AC_{TVPP}$ is based on an AC ratio, ACR, and the hematocrit of the donor.

Once the TVPP is determined, the plasmapheresis procedure is commenced, with whole blood being drawn from the donor, mixed at a specified ratio with anticoagulant, and then separated into plasma, red blood cells, and other cellular components. Once the TVPP has been collected, as determined by, e.g., a weigh scale associated with a plasma collection container, the withdrawal of whole blood from the donor ceases, and the red blood cells and other cellular components are returned to the donor.

In a seventh aspect, in determining the target amount for the plasma product to be collected, the hematocrit of the donor may be determined prior to the collection phase of each cycle, either by calculation or on the basis of a signal from a sensor or the like that is indicative of the donor's hematocrit. Further, the amount of plasma product in the plasma collection container may be determined by: e.g., a weigh scale associated with the plasma collection container or an optical sensor that directly measures the volume.

In other aspects, a method is provided for operating a plasmapheresis system to collect a plasma product volume that comprises the maximum allowable volume/weight of raw plasma in accordance with the limits set forth in the FDA nomogram based on the weight of the donor.

In order to collect the maximum volume/weight of raw plasma permitted by the FDA nomogram, a modified nomogram is provided that utilizes the donor's hematocrit to calculate a target volume/weight for a plasma product having the maximum volume of raw plasma permitted by the FDA nomogram. A calculated volume/weight of raw plasma is compared to the maximum volume/weight for the raw plasma permitted by the FDA nomogram. If the calculated volume/weight of raw plasma is less than the maximum permitted volume/weight, the volume/weight of the plasma product to be collected is adjusted upward from the maximum volume/weight permitted by the FDA nomogram for the plasma product by an amount equal to the difference plus the additional amount of anticoagulant that is added to process the additional volume/weight of plasma.

Thus, with the knowledge of the donor's hematocrit and the instrument's AC ratio, the volume of additional raw plasma that may be safely collected from the donor consistent with the limits set forth in the FDA nomogram is determined, and then the total volume/weight of plasma product to be collected based on the weight of the donor set forth in the FDA nomogram is adjusted accordingly.

Typically, plasmapheresis procedures involve sequential cycles of alternating phases, one in which whole blood is withdrawn from the donor and the plasma separated and collected, and the other in which the separated red blood cells and any other non-RBC cellular components are returned to the donor. The donor's hematocrit will change during the course of the plasmapheresis procedure, thus affecting the amount of anticoagulant in the plasma product collected from one cycle to the next.

Consequently, in the first aspect of the disclosure, before the commencement of the subsequent extraction/separation phase, a new hematocrit value for the donor is determined, and the target volume/weight of plasma product for the procedure is recalculated before the commencement of each extraction/separation phase to ensure that the maximum amount of raw plasma permitted by the FDA nomogram is collected.

In another aspect, a further method for collecting a volume of plasma during an apheresis procedure is provided. The steps of the method comprise: determining a total whole blood volume $V_b$ for the donor; determining a volume of raw plasma ($V_{RP}$) that may be collected from the donor based on $V_b$; determining a target volume of plasma product ($V_{PP}$) to be collected, wherein VF is equal to the volume of raw plasma ($V_{RP}$) to be collected plus a volume of anticoagulant ($V_{AC}$) that is added to the $V_{RP}$ during the apheresis procedure, such that $V_{PP}=V_{RP}*K$, where K=(ACR*(1−Hct/100)+1)/(ACR*(1−Hct/100)), based on an anticoagulant ratio (ACR, defined as the ratio of donor blood volume to anticoagulant volume for donor blood having no anticoagulant) established for the procedure and a Hct of the donor; withdrawing whole blood from the donor; adding anticoagulant to the whole blood in an amount consistent with the ACR; separating plasma product from the whole blood; and transferring the plasma product to a collection container until the volume of plasma product in the collection container reaches $V_{PP}$. Because the plasmapheresis procedure comprises multiple extraction/separation and return phases, the $V_{PP}$ for the procedure is recalculated before each extraction/separation phase is commenced, based on a value for the hematocrit of the donor determined prior to the start of each draw phase, and the target volume for the plasma product adjusted accordingly. Alternatively. $V_{RP}$ may be determined based on a calculated value for the donor's total plasma volume, based on $V_b$ and the donor's hematocrit.

In another aspect, a method for determining a volume of plasma product ($V_{PP}$) that may be collected during an apheresis procedure is provided, wherein $V_{PP}$ is equal to a volume of raw plasma ($V_{RP}$) that may be collected plus a volume of anticoagulant ($V_{AC}$) that is added to the $V_{RP}$ during the apheresis procedure. The steps of the method comprise: determining a weight ($W_{kg}$) and sex (M or F) of the donor, determining a hematocrit (Hct) for the donor; determining the volume of raw plasma ($V_{RP}$) that may be collected based on the weight ($W_{kg}$) and sex (M or F) of the donor; determining a ratio K between the VP and the $V_{RP}$, such that $K=V_{PP}/V_{RP}$, based on an anticoagulant ratio (ACR) and the Hct of the donor; determining $V_{PP}$, such that $V_{PP}=V_{RP}*K$. Further, $K=(ACR*(1-Hct/100)+1)/(ACR*(1-Hct/100))$. After $V_{PP}$ is determined, whole blood is withdrawn from the donor; anticoagulant is added to the whole blood in an amount consistent with the ACR; plasma product is separated from the whole blood; and plasma product is transferred to a collection container. After a desired amount of whole blood has been withdrawn from the donor, the red blood cells are returned to the donor. Then, the Hct of the donor and $V_{PP}$ are determined prior to each draw phase.

In a related aspect, the draw and separation steps are repeated until the volume of plasma product in the collection container reaches $V_{PP}$.

In a related aspect, the donor's hematocrit subsequent to the first collection phase may be calculated by a volume balance, assuming that the donor's quantity of red blood cells is the same at the start of each draw cycle, while the total volume of blood decreases from one cycle to the next in an amount equal to the amount of raw plasma collected. Alternatively, the donor's hematocrit at the start of each draw cycle can be measured by an optical or other sensor.

In a further aspect, the volume of raw plasma that may be collected from a particular donor may be determined by any one of several different means. Such means include, e.g., the FDA nomogram, taking into account only the donor's weight; a modified FDA nomogram, further taking into account the donor's hematocrit, and taking a fraction of a total blood volume or total plasma volume calculated for a particular donor. The total blood volume or total plasma volume may be determined using, for example, Nadler's equations, Gilcher's Rule of Five, tables provided by the International Council for Standardization in Haematology (ICSH), or any other generally accepted method using the donor's height, weight, sex, and age, consistent with the safety and comfort of the donor.

In another aspect, an automated system for separating plasma from whole blood is provided that comprises a reusable hardware component and a disposable kit. The disposable kit further comprises i) a separator for separating whole blood into a plasma fraction and a concentrated cell fraction, the separator having an input having a blood line integrally connected thereto for transporting whole blood from a donor to the separator, a plasma output port integrally connected to a plasma collection container by a plasma line, and a concentrated cell outlet port integrally connected to a reservoir for receipt of concentrated cells prior to reinfusion to the donor; ii) a donor line terminating in a venipuncture needle for transporting whole blood from a donor to the blood line, iii) an anticoagulant line integrally connected to the blood line and configured to be connected to a source of anticoagulant for transporting anticoagulant to the donor line, and iv) a reinfusion line for transporting concentrated cells from the reservoir to the donor line.

The reusable hardware component further comprises i) a first peristaltic pump for delivering anticoagulant at a controlled rate into the blood line during a collection phase, ii) a second pump for delivering anticoagulated whole blood to the separator during the collection phase and for returning concentrated cellular components during a reinfusion phase, iii) a third pump for delivering concentrated cellular components from the separator to the reservoir during the collection phase, iv) a clamp associated with each of the blood line, plasma line, and reinfusion line, v) a weigh scale for weighing each of the plasma collection container, the reservoir and the source of anticoagulant, and vi) a programmable controller comprising a touch screen for receiving input from an operator, the programmable controller configured to receive a signal from each of the weigh scales and to automatically operate the first, second and third pumps and the clamps to separate whole blood into a plasma fraction and a concentrated cell fraction during the collection phase and to return concentrated cells to the donor during the reinfusion stage. The programmable controller is further configured to determine a target amount for the plasma product to be collected in the plasma collection container in accordance with any of the methods described herein, and to terminate the collection phase upon receiving a signal that the amount of plasma product in the plasma collection container equal to the target amount of the plasma product determined by the controller. In determining the target amount for the plasma product to be collected, the controller may be configured to calculate the hematocrit of the donor prior to the collection phase of each cycle. Alternatively, or additionally, the controller may receive a signal from a sensor or the like that is indicative of the donor's hematocrit. Further, the amount of plasma product in the plasma collection container may be determined by, e.g., the weigh scale associated with the plasma collection container or an optical sensor that directly measures the volume.

BRIEF DESCRIPTION OF THE DRAWINGS

FIG. 7 is a table that shows the volume of pure plasma, based on donor hematocrit, that is contained within a plasma product volume limit set by the FDA nomogram using a 1:16 ratio of anticoagulant to whole blood.

FIG. 8 is a table that shows the volume of "unclaimed" pure plasma in the plasma product based on the difference between the values set forth in FIG. 7 and the maximum volume of pure plasma that may be collected based on the FDA nomogram.

FIG. 9 is a table that shows the volume of plasma product that may be collected from a donor, based on the donor's weight and hematocrit, that results in the maximum permissible volume of pure plasma permitted by the FDA nomogram.

FIG. 10 is a table showing the inputs to a programmable controller for performing a hypothetical plasmapheresis procedure in accordance with the method of the present application.

FIGS. 11a, 11b comprise a table, broken into two parts illustrating how the donor's hematocrit increases over the course of a hypothetical plasmapheresis procedure based on the inputs from the table of FIG. 10, and resulting in an increase in the total collection volume of plasma product necessary to collect the target volume of pure plasma.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill. Various aspects of the system and method are described in greater detail in US 2020/0147289, which is incorporated herein by reference.

In the context of the present application, plasmapheresis is performed on an automated system comprising a hardware component, generally designated 10, and a disposable set, generally designated 12, to collect plasma to be processed as source plasma. With reference to FIGS. 1-5, and as described in greater detail below, the disposable set 12 consists of an integrally connected separator, containers, and tubing to transport blood and solutions within a sterile fluid pathway.

Figure 1:
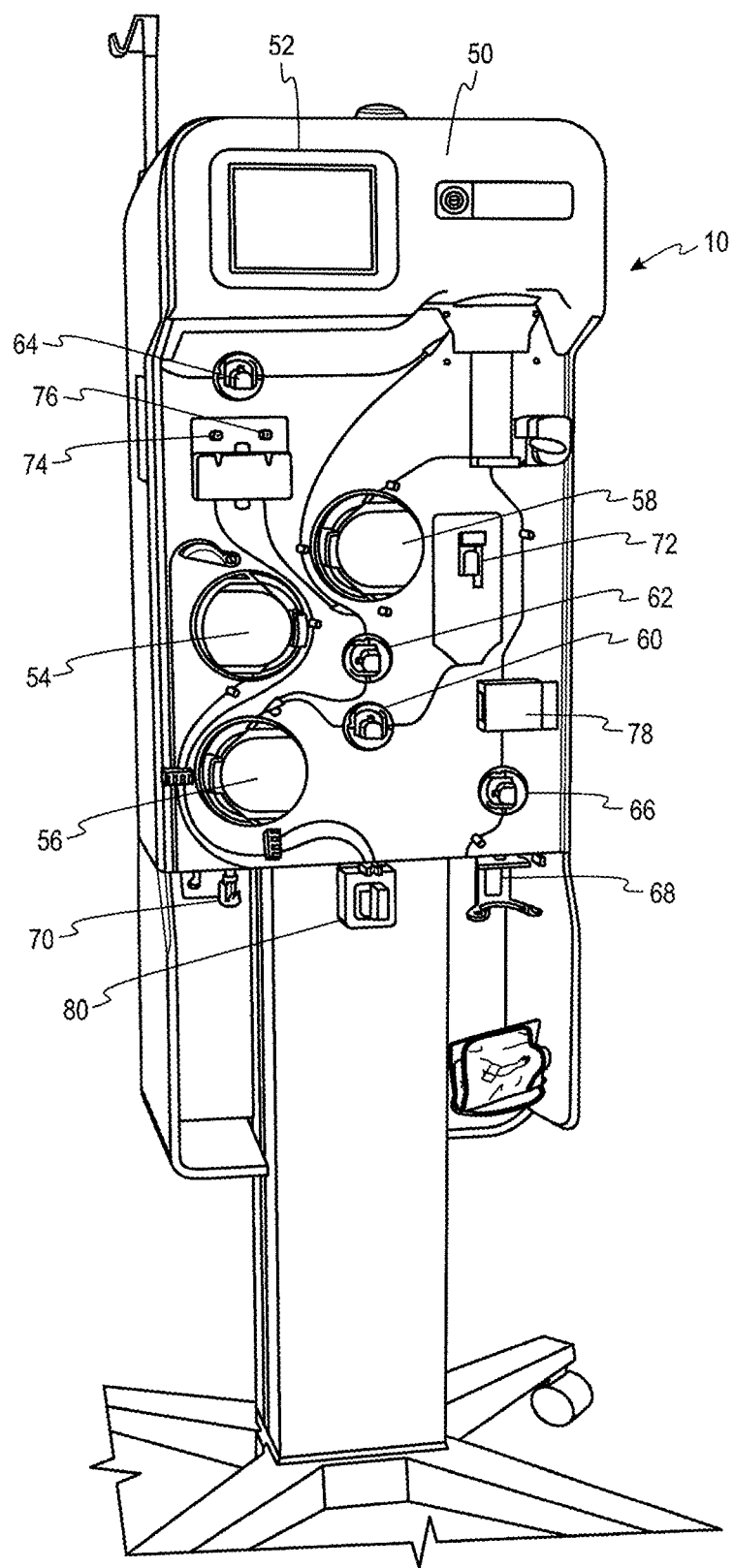
FIG. 1 is a perspective view of an exemplary plasmapheresis instrument suitable for use in the system and method of the present application.
Figure 2:
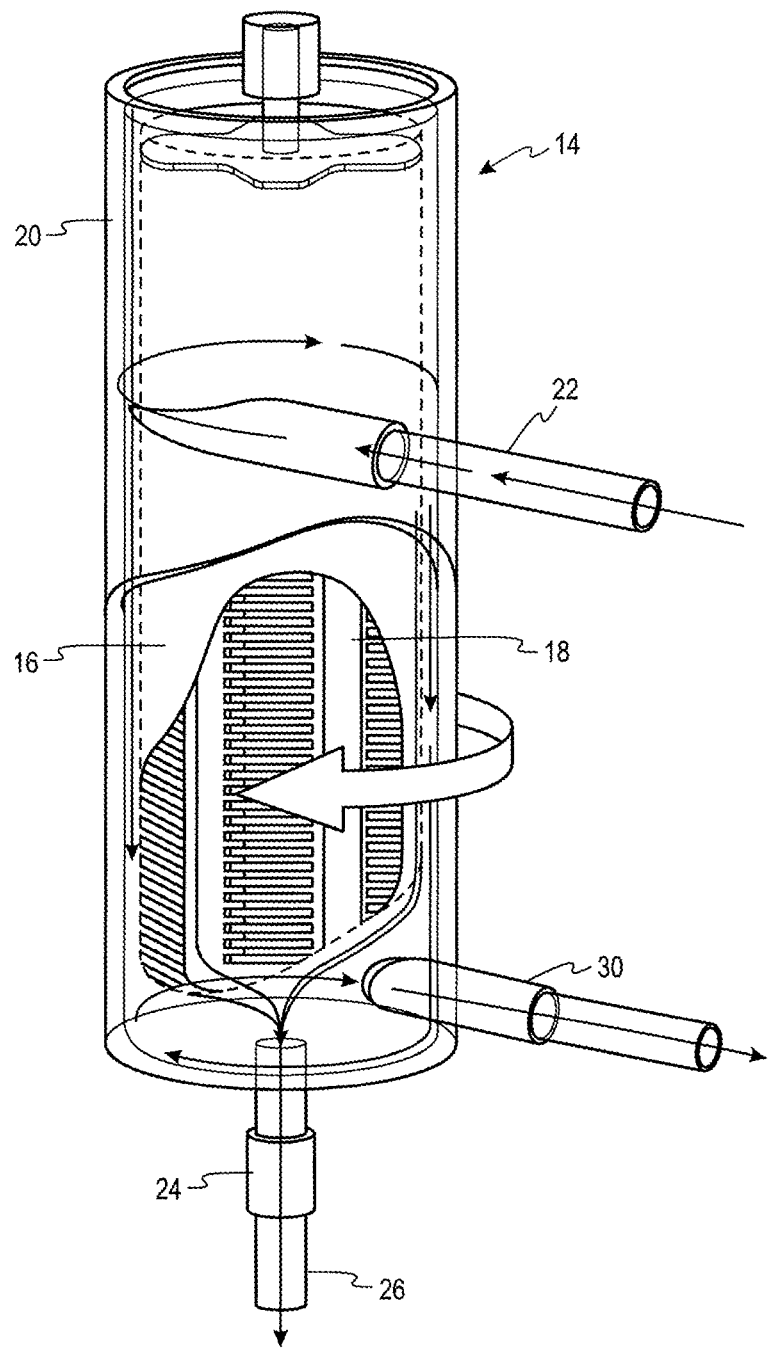
FIG. 2 is a perspective view of a spinning membrane separator of the type incorporated in a disposable set, with portions broken away to show detail, usable with the plasmapheresis system of FIG. 1.
Figure 3:
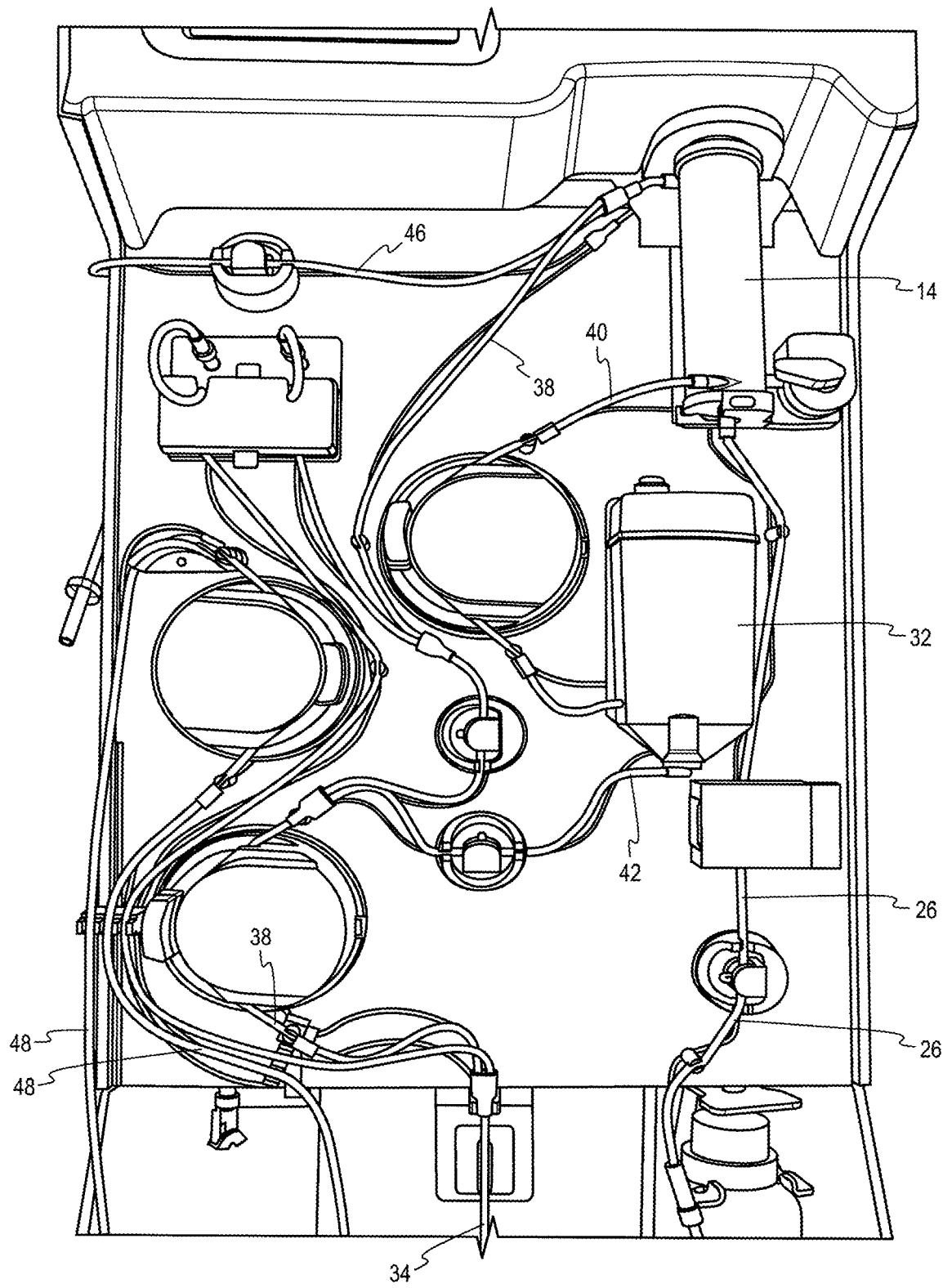
FIG. 3 is a perspective view of the front panel of the plasmapheresis system of FIG. 1 showing the components of the disposable set that are mounted thereto.
Figure 4:
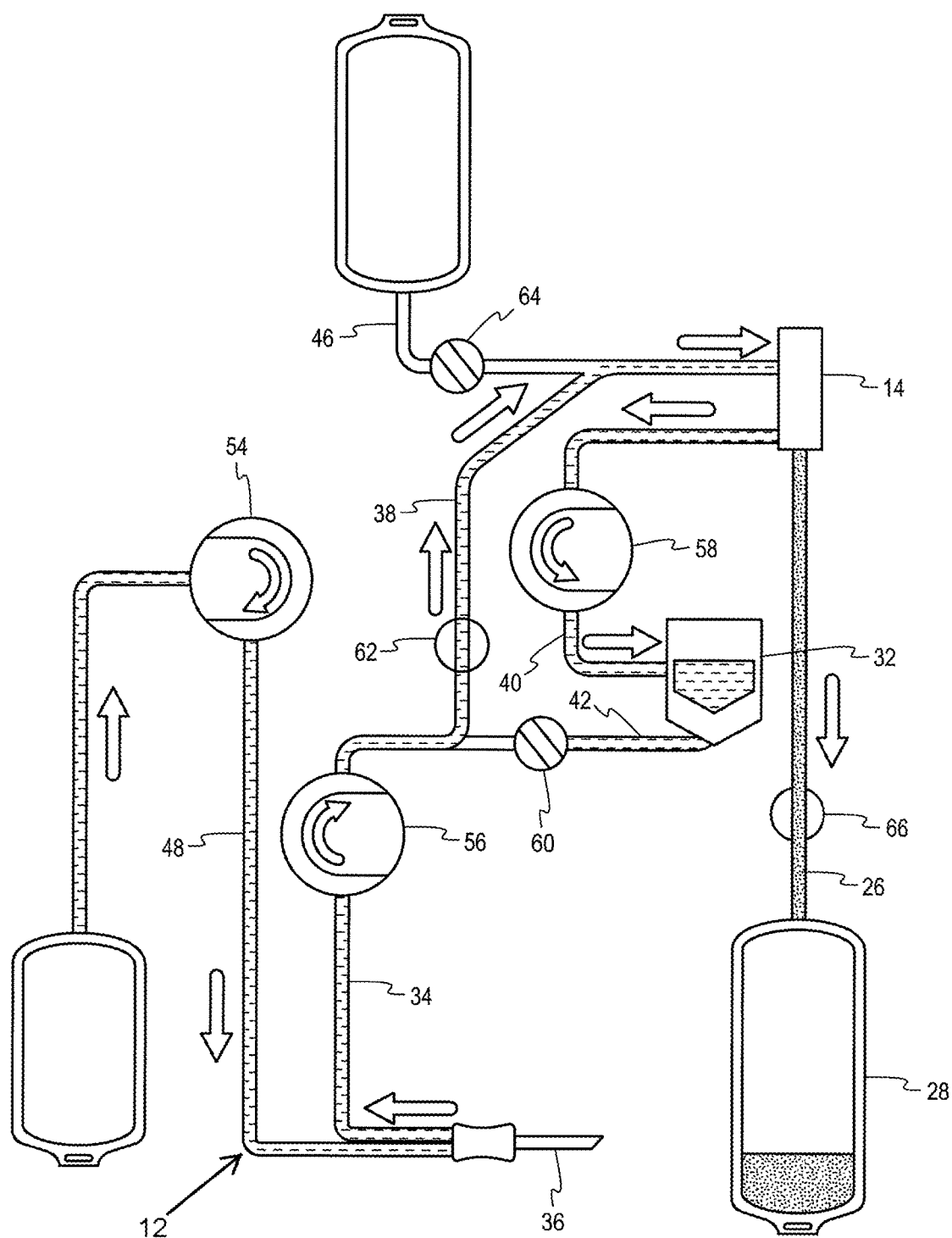
FIG. 4 is a schematic view showing operation of the plasmapheresis system in the collection phase.

The separator 14, best seen in FIG. 2, has a spinning membrane filter 16 mounted to a rotor 18 for rotation within a case 20 to separate blood into components. A detailed description of a spinning membrane separator may be found in U.S. Pat. No. 5,194,145 to Schoendorfer, which is incorporated herein by reference. As can be appreciated, in a different system, separation of the whole blood may be accomplished by centrifugation. See, e.g., U.S. Pat. No. 5,360,542 to Williamson et al.

During plasmapheresis, anticoagulated whole blood enters the separator 14 through a whole blood input port 22. The plasma is separated by the spinning membrane filter and then passes out of a plasma output port 24, through a plasma line 26, and into a plasma collection container 28. Concentrated cells are pumped out of a concentrated cell output port 30 into a reservoir 32, where the cells remain until reinfusion to the donor.

The disposable set 12 also includes tubing lines for introducing whole blood from the donor into the system during collection and returning concentrated cells to the donor during reinfusion (donor line 34, which terminates in the venipuncture needle 36), and for transporting anticoagulated whole blood to the separator (blood line 38), concentrated cells into the reservoir (cell line 40), concentrated cells from the reservoir to the donor line (reinfusion line 42), plasma into the plasma collection container (plasma line 44), saline (saline line 46), and anticoagulant (AC line 48).

The hardware component 10 includes a programmable controller 50 and touch screen 52 with a graphical user interface ("GUI") through which the operator controls the procedure. For example, the GUI permits entry of any of a donor ID, donor sex, donor height, donor weight, donor age, donor hematocrit/hemoglobin; a target saline infusion volume (if a saline protocol is selected), and a target plasma volume. The touch screen 52 also enables the operator to gather status information and handle error conditions.

Three peristaltic pumps are located on the front panel of the hardware component 10, including an AC pump 54, a blood pump 56, and a cell pump 58. The AC pump 54 delivers anticoagulant solution (AC) at a controlled rate into the blood line 38 as whole blood enters the set from the donor. The blood pump 56 delivers anticoagulated whole blood to the separator during the collection phase of the procedure and returns concentrated cellular components and, if desired, replacement fluid to the donor during the reinfusion phase of the procedure. The cell pump 58 delivers concentrated cellular components from the separator 14 to a reservoir during the collection phase.

The front panel also includes four clamps into which tubings from the disposable set 12 are installed, including a reinfusion clamp 60, a blood clamp 62, a saline clamp 64, and a plasma clamp 66. The reinfusion clamp 60 closes to block the reinfusion line (42) during the collection phase (FIG. 5) and is open during the reinfusion phase (FIG. 5) to allow the blood pump to reinfuse the concentrated cellular components from the reservoir 32 to the donor. The blood clamp 62 opens during the collection phase to allow anticoagulated whole blood to be pumped to the separator 14 and closes during the reinfusion phase to block the blood line 38. The saline clamp 64 closes to block the saline line 46 during the collection phase and during reinfusion of the separated cellular components. If saline is to be used as a replacement fluid, the saline clamp 64 opens during the reinfusion phase. The plasma clamp 66 opens during the collection phase to allow plasma to flow into the plasma collection container 28 and closes during the reinfusion phase.

The hardware component 10 includes three weigh scales to monitor the current plasma collection volume (scale 68), the AC solution volume (scale 70), and the concentrated cellular content volume (scale 72). The system also includes various sensors and detectors, including a venous pressure sensor 74, a separator pressure sensor 76, optical blood detectors 78, and an air detector 80.

Figure 5:
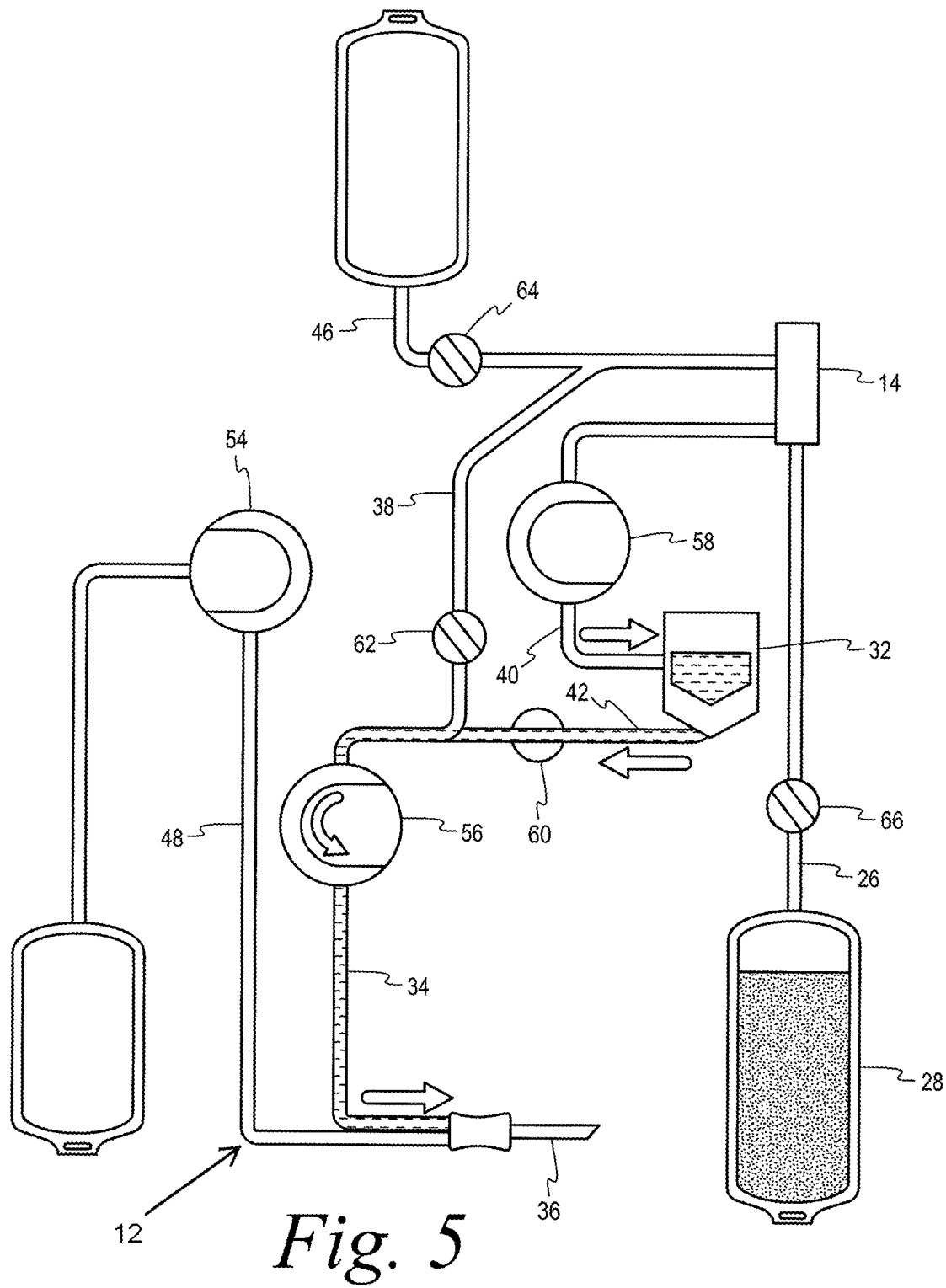
FIG. 5 is a schematic view showing operation of the plasmapheresis system in the reinfusion phase.

The donor is connected to the system throughout the procedure. As illustrated, the disposable set 12 includes a single venipuncture needle 36, through which whole blood is drawn from the donor in a collection phase (FIG. 4) and concentrated cells are returned to the donor in a reinfusion stage (FIG. 5). As noted above, the plasmapheresis procedure may comprise a plurality of cycles each having a collection/separation phase followed by a return or reinfusion phase. During the collection phase, the whole blood is separated into plasma and concentrated cells. The disposable set includes a plasma collection container 28 for receipt of the separated plasma and a reservoir 32 for receipt of the concentrated cells. During the reinfusion phase, the concentrated cells from the reservoir 32 are reinfused to the donor through the venipuncture needle 36. Plasmapheresis performed with a single venipuncture needle 36 may involve multiple cycles of collection and reinfusion.

Returning to FIG. 4, during the collection phase, anticoagulant solution (AC) is pumped at a controlled rate and mixed with whole blood as it enters the disposable set 12. The anticoagulated blood is pumped to the separator 14, where plasma is separated from the cellular components and directed to the plasma collection container 28.

The cellular components are pumped from the separator 14 to the reservoir 32. The collection phase stops when the reservoir 32 reaches an expected volume of concentrated cells or if the target plasma collection volume has been achieved.

Then, the reinfusion phase begins. With reference to FIG. 5, during the reinfusion phase, the blood pump 56 reverses direction and pumps the concentrated cells from the reservoir 32 back to the donor through the apheresis needle 36. If a saline protocol was selected, by which saline is returned to the donor as a replacement fluid for the collected plasma, the final reinfusion phase is followed by saline infusion.

The automated plasma collection device is configured to collect a volume/weight of anticoagulated plasma (i.e., the plasma product) having the maximum volume/weight of raw plasma permitted for the donor under the limits set forth in the FDA nomogram. In order to maximize the volume of raw plasma comprising the plasma product, the device is programmed with a nomogram that accounts for the donor's hematocrit. With the knowledge of the donor's hematocrit and the instrument's AC ratio, the total volume/weight of plasma product to be collected can be determined such that the plasma product includes the maximum volume/weight of raw plasma fraction that may be collected from a donor, consistent with the limits for total volume/weight of raw plasma set forth in the FDA nomogram. By having the computations programmed into the controller, the likelihood of operator error is diminished in comparison to the off-line calculation of the collection volume that is then entered into the instrument.

During plasmapheresis, when anticoagulant is mixed with whole blood as it is drawn from the donor, the anticoagulant is evenly distributed within the pure/raw plasma in the blood. However, the amount of pure/raw plasma in the whole blood is dependent on the hematocrit (Hct) of the whole blood. The following relationships are established:

Volume of RBC=Volume of Whole Blood*Hct/100.     [1]

Volume of Pure/Raw Plasma=Volume of Whole Blood*(1−Hct/100).     [2]

When anticoagulant is mixed with the whole blood, it may be metered at an AC Ratio (ACR) of 16 parts of whole blood to 1 part of AC, or at 1 part of whole blood to 0.06 parts of AC.

ACR=Volume of Whole Blood/Volume of Anticoagulant(the donor blood having no anticoagulant).     [3]

(This yields a slightly different result from the FDA nomogram, which, as noted above, standardizes the volume of anticoagulant that may be added to a 1:16 ratio of anticoagulant to anticoagulated blood, or 0.06 parts anticoagulant to 1 part anticoagulated blood.)

Volume of Anticoagulated Blood=Volume of Anticoagulant+Volume of Whole Blood.     [4]

Combining equations gives:

Volume of Pure/Raw Plasma=ACR*Volume of Anticoagulant*(1−Hct/100).     [5]

Since the red cells are given back to the donor:

Volume collected Plasma Product=Volume of Pure/Raw Plasma+Volume of Anticoagulant.     [6]

Equations [5] and [6] can be combined to calculate the amount of anticoagulant in a given amount of collected plasma:

Volume of Anticoagulant=Volume of collected Plasma Product/(1+ACR*(1−Hct/100)).     [7]

Further

Volume of collected Plasma Product=Volume of Pure/Raw Plasma*K, where K=(ACR*(1−Hct/100)+1)/(ACR*(1−Hct/100)).     [8]

In view of the relationships expressed in the equations above, the volume of pure/raw plasma contained within the volume of plasma product permitted under the FDA nomogram can be determined based upon the hematocrit of the donor. The results of such calculations are set forth in FIG. 7, which shows the volume of pure/raw plasma based on donor hematocrit that is contained within a plasma product volume limit set by the FDA nomogram.

As can be appreciated with reference to FIG. 7, for donors weighing from 110 to 149 lbs. (for whom the maximum plasma product volume per the FDA nomogram is 690 mL), if the donor has a hematocrit of 42 or greater, the volume of raw plasma collected is less than the 625 mL permitted by the FDA nomogram. The situation is similar for donors having a weight of 150 to 174 lbs. (for whom the maximum plasma collection volume per the FDA nomogram is 825 mL) and for donors having a weight of 175 lbs. and up (for whom the maximum plasma collection volume per the FDA nomogram is 880 ml) when the donor's hematocrit is 40 or greater.

The table set forth in FIG. 8 presents the volume of "unclaimed" raw plasma in the plasma product based the difference between the values set forth in FIG. 7 and the maximum volume of pure/raw plasma that may be collected based on the FDA nomogram. Thus, as shown in the table set forth in FIG. 9, the plasma product collected from any particular donor may be adjusted from that set forth in the FDA nomogram by an amount corresponding to the amount of "unclaimed" pure/raw plasma set forth in FIG. 8 plus the amount of anticoagulant needed to process the additional volume.

Alternatively, the volume of plasma product to be collected may be calculated by first determining a weight and hematocrit (Hct) for the donor; determining the volume of raw plasma ($V_{RP}$) that may be collected based on the weight of the donor ($W_{kg}$); determining a ratio K between the $V_{PP}$ and the $V_{RP}$, such that $K=V_{PP}/V_{RP}$, based on an anticoagulant ratio (ACR; 1:16 or 0.06:1, per the FDA nomogram) and the Hct of the donor; and determining $V_{PP}$, such that $V_{PP}=V_{RP}*K$. Further, $K=(ACR*(1-Hct/100)+1)/(ACR*(1-Hct/100))$.

In a further alternative, the volume of plasma product that is to be collected ($V_{PP}$) may be calculated by first determining the weight ($W_{kg}$) and hematocrit (Hct) of the donor; determining the volume of raw plasma ($V_{RP}$) that may be collected based on the weight of the donor ($W_{kg}$); determining the volume of anticoagulant to be added ($V_{AC}$) based on the anticoagulant ratio (ACR; 1:16 or 0.06:1, per the FDA nomogram) and the hematocrit of the donor such that $V_{AC}=V_{RP}*(ACR*(1-Hct/100))$; and determining the collection volume such that $V_{PP}=V_{RP}+V_{AC}$.

In keeping with one aspect of the disclosure, the automated plasma collection device is configured to collect a volume/weight of plasma product (pure plasma+anticoagulant) having a volume/weight of pure plasma permitted for the donor as determined by either of the two methods set forth in greater detail below.

Figure 6A:
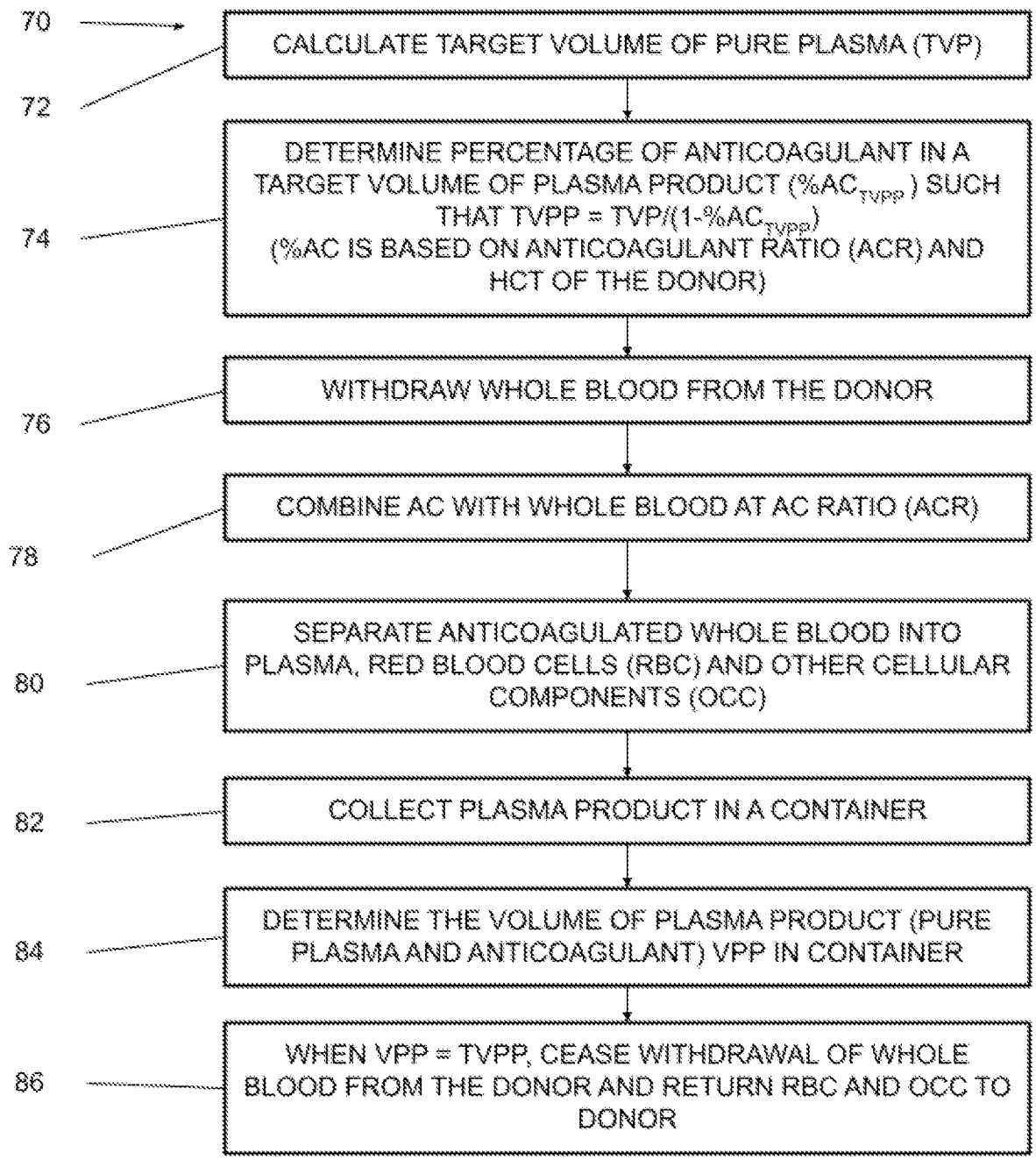
FIGS. 6a and 6b are flow charts showing the steps of methods used in the present application for collecting a target volume of pure plasma.

With reference to FIG. 6a, a first method (70) for collecting a target volume of plasma product, TVPP, is illustrated. In the method, the target volume of plasma product (TVPP) is determined by first calculating a target volume of pure plasma to be collected (TVP) based on the weight of the donor (Step 72) and then determining a percentage of anticoagulant in the target volume of plasma product to be collected (% $AC_{TVPP}$) based on the pre-determined anticoagulant ratio (ACR) and the hematocrit of the donor, wherein the TVPP=TVP/(1-% $AC_{TVPP}$) (Step 74). In this method no intervening calculation is required of either a total blood volume or a total plasma volume of the donor prior to determining the target collection volume of plasma for the donor, though, in alternate embodiments, such calculations may be included.

Various methods may be used for determining a target volume of pure plasma that may be collected directly from the weight of the donor. For example, the weight of the donor may be multiplied by an established constant "$K_1$" (such as 10 mL/kg). Alternatively, the weight of the donor may be segregated into weight categories or ranges (e.g., at least three categories, at least six categories, etc.), with a fixed volume established for each category (as in the FDA nomogram discussed above, in which the ranges of donor weight are divided into three categories).

The anticoagulant ratio, ACR, may be defined in one of two different ways. In a first way, ACR is the ratio of the amount of whole blood to the amount of anticoagulant (ACR=WB/AC). In a second way, ACR is the ratio of volume of whole blood plus the volume of anticoagulant to the volume of anticoagulant (ACR=(WB+AC)/AC). If ACR=WB/AC, then the percent of anticoagulant in the target volume of plasma product, % $AC_{TVPP}$, is determined according to the following equation: % $AC_{TVPP}=1/(1+ACR(1-Hct))$, with ACR and Hct being expressed as percentages. If ACR=(WB+AC)/AC, then the percent of anticoagulant in the target volume of plasma product, % $AC_{TVPP}$, is determined according to the following equation: % $AC_{TVPP}=1/(1+(ACR-1)(1-Hct))$. The ACR may be expressed as either a ratio or a percentage, and may vary from 7:1 to 20:1, or from about 5% to 14%. An exemplary ACR is 16:1, or 6.25%.

Returning to FIG. 6a, once the TVPP has been determined, as described above, whole blood is withdrawn from the donor (Step 76) and combined with anticoagulant based on a predetermined ratio, ACR (Step 78). Anticoagulated whole blood is then introduced into separator 14, where it is separated into plasma and concentrated (red blood) cells (Step 80). Plasma product (pure plasma and anticoagulant) is collected in plasma collection container 28 (Step 82) while separated red blood cells are collected in reservoir 32. As the plasma product is being collected, the volume of plasma product, $V_{PP}$, (pure plasma and anticoagulant) in the plasma container is determined (Step 84). When the $V_{PP}$ equals the Target volume of plasma product (TVPP), withdrawal of whole blood ceases and any remaining blood components (such as red blood cells) are returned to the donor (Step 86).

Figure 6B:
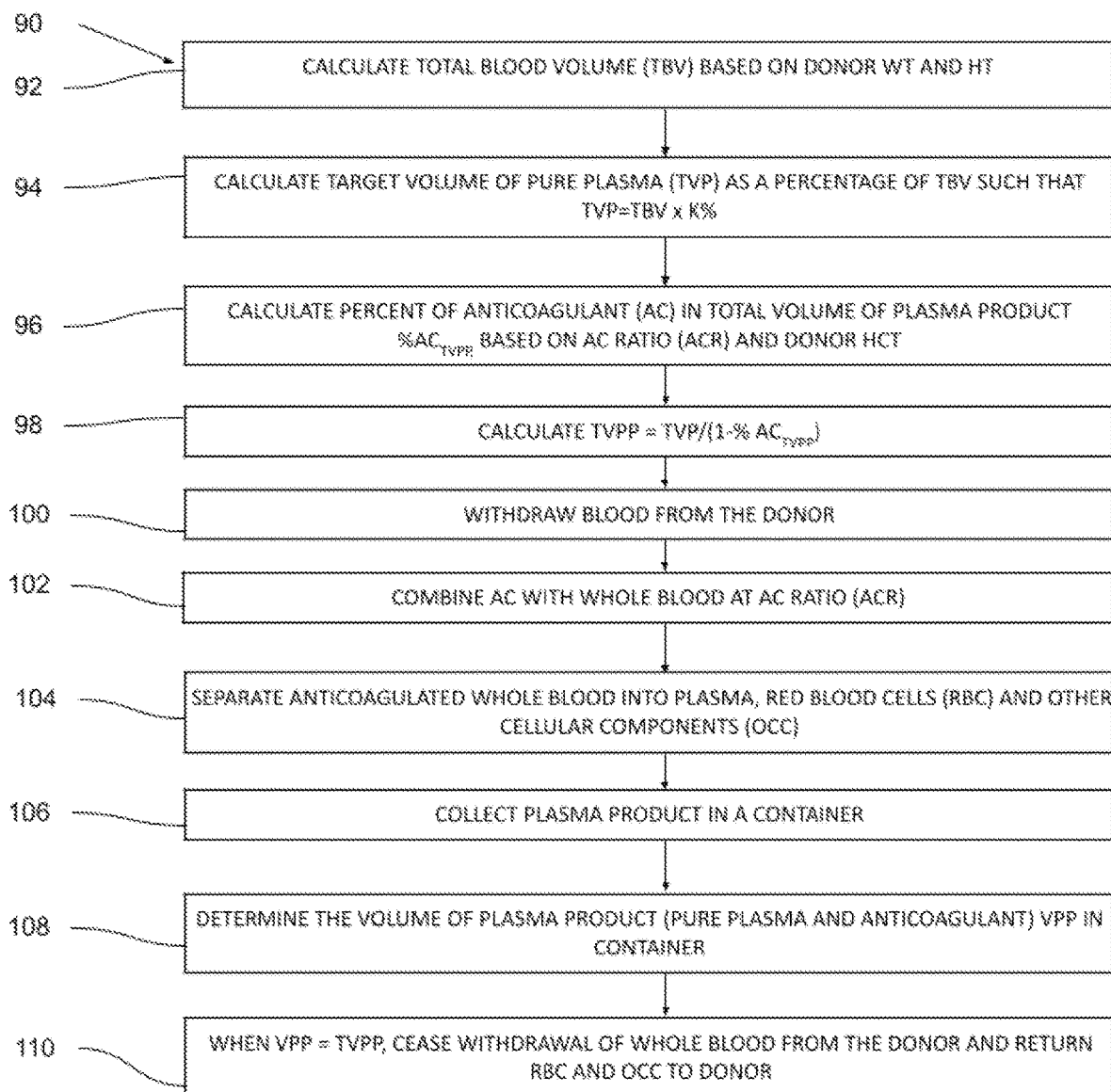

With reference to FIG. 6b, a second method (90) for collecting a target volume of plasma product, TVPP, is illustrated. In this method, the target volume of plasma product, TPPV, is determined by first calculating a total blood volume of the donor (TBV) based on the weight and height of the donor (Step 92), calculating a target volume of pure plasma product to be collected, TVP, as a percentage of the TBV (Step 94), and calculating a percentage of anticoagulant in the target volume of plasma product to be collected (% $AC_{TVPP}$) based on the pre-determined anticoagulant ratio (ACR) and the hematocrit of the donor (Step 96), and calculating TVPP wherein TVPP=TVP/(1-% $AC_{TVPP}$) (Step 98). The % $AC_{TVPP}$ may be determined as described above in connection with the first method. In this method no calculation of a total plasma volume of the donor is required to determine the target collection volume of plasma for the donor.

A donor's plasma volume may be estimated based on the donor's total blood volume, and a volume of plasma that may be harvested consistent with donor safety and comfort may be based on this estimation. Methods utilizing donor parameters are commonly used estimate a donor's total blood volume. The donor's total blood volume may be determined using one or more of Lemmens equation (that uses the donor's body mass index to determine a total blood volume), Nadler's equations (that take into account the height, sex and weight of the donor), Gilcher's Rule of Five (that takes into account sex, weight and morphology (obese, thin, normal or muscular), or the standards of the International Counsel for Standardization in Haematology ("ICSH") as set forth in Br. J. Haem. 1995, 89:748-56) (that consider the height, weight, age, and sex of the donor). Any other methodology for determining donor's total blood volume may also be used. In another embodiment, a plurality of such methodologies may be used and the average, mean, or a weighted average of the methodologies may be taken as the donor's total blood volume. For example, once the donor's total blood volume is determined, the donor's plasma volume may be estimated by multiplying the total blood volume by a constant "$K_2$", where or $K_2$ equals (1-Hct of the donor).

From an analysis of demographic, examination, and laboratory data from the 2015-2016 National Health and Nutrition Examination Survey, in which sex, age, height, weight, pregnancy data and hematocrit were extracted, presented in Pearson et al., Interpretation of measured red cell mass and plasma volume in adults: Expert Panel on Radionuclides of the International Council for Standardization in Haematology, British J. Haematology, 89: 748-756 (1995), (upon which the ICSH recommended formulae were derived), it has been determined that for donors having certain characteristics (namely low weight females with high hematocrits), up to 36% of the available plasma may be collected while staying within current regulations. Plasmapheresis procedures with such donors have been carried out routinely without adverse reactions, and thus are considered safe. This suggests that up to 36% of a donor's available plasma can be safely collected in a plasmapheresis procedure.

Given that only negative deviations of a donor's true blood volume from a predicted/calculated total blood volume present a potential risk, a further adjustment downward of the harvestable volume of plasma may be appropriate. Based on a consideration of the deviation between the calculated blood volume as determined in Pearson et al., cited above.

Thus, the total blood volume of the donor (TBV) may be calculated based on the weight (WA) and height (Ht) of the donor to calculate a body mass index for the donor (BMI)

such that TBV=70/sqrt(BMI/22), where BMI=Wt/Ht$^2$, and where Ht is in meters and Wt is in kilograms (Lemmens equation). See, *"Estimating Blood Volume in Obese and Morbidly Obese Patients,"* Lemmens et al., Obesity Surgery 16, 2006, pp. 773-776.

Alternatively, the total blood volume of the donor (TBV) may be calculated based on the weight (Wt), height (Ht) and sex (Male or Female) of the donor such that TBV= (0.3669*Ht$^3$)+(0.03219*Wt)+0.6041 for Males and TBV= (0.3561*Ht$^3$)+(0.03308*Wt)+0.1833 for Females, where Ht is in meters and Wt is in kilograms (Nadler's formula).

The percentage by which TBV is multiplied to obtain TVP (and, ultimately TVPP) is selected to maximize the volume of pure plasma that is collected from the donor consistent with donor comfort and safety. The percentage ranges in various embodiments may be variously between approximately 1% and 15% of TBV, at least 15%, less than 18%, between about 15% and 17%, about 12%, about 16% or about 18%. The TVPP may also be subject to a maximum volume of, e.g., 1000 mL or 1050 mL to be collected regardless of the donor's TBV.

An adjustment, Vc, may be made to the calculated volume of whole blood TBV before calculating the target volume of pure plasma TVP, such that TVP=0.36(1−Hct)(TBV−Vc), where Vc=523 mL, based on a regression analysis of the experimental blood volume data presented in Retzlaff et al., *Erythrocyte Volume, Plasma Volume, and Lean Body Mass in Adult Men and Women*, J. Haematology, 33, 5:649-667 (1969). There is a 95% confidence that an individual's predicted blood volume will differ not more that 20.5%. Thus, a scaling factor of 0.795 may be applied to determination of harvestable raw plasma being 36% of the donor's total plasma volume described above, so that 28.6% of a donor's calculated volume of raw plasma may be harvested, consistent with donor safety and comfort.

Retuning to FIG. 6*b*, once the TVPP has been determined, as described above (based on the TBV), whole blood is withdrawn from the donor (Step 100) and combined with anticoagulant based on a predetermined ratio (Step 102). Anticoagulated whole blood is then introduced into separator 14 where it is separated into plasma and concentrated (red blood) cells (Step 104). Plasma product (pure plasma and anticoagulant) is collected in plasma collection container 28 (Step 106) while separated red blood cells are collected in reservoir 32. As the plasma product is being collected, the volume of plasma product, VPP, (pure plasma and anticoagulant) in the plasma container is determined (Step 108). When the VPP equals the Target volume of plasma product (TVPP), withdrawal of whole blood ceases and any remaining blood components (such as red blood cells) are returned to the donor (Step 110).

Thus, the collection volume (the volume of plasma product) is determined based on the volume of raw plasma volume that may be collected from a particular donor, the donor's hematocrit, and the fixed anticoagulant ratio (ACR). Consequently, this methodology allows for more consistent control for the raw plasma volume of the donor, which is the variable most related to donor safety.

In an exemplary method, the operator enters into the system controller the collection volume for the plasma product for the particular donor, based on the target volume of raw plasma that may be harvested. The target plasma collection volume may be as set forth in FIG. 9, based on the donor's weight and hematocrit for the initial collection phase, or by any of the other methods as set forth above. Alternatively, the controller is configured to calculate the target plasma product collection volume for the initial collection phase in accordance with a methodology such as those described above upon the operator entering, e.g., the donor's weight and hematocrit, and/or any of the additional donor-specific information (such as the donor's sex, height and age) required by the methodologies used for determining a donor's total blood volume, total plasma volume, and the target volume of harvestable plasma that may be collected.

In practice, the operator enters into the system controller the collection volume for the plasma product for the particular donor, based on the target volume of raw plasma that may be harvested. The target plasma collection volume may be as set forth in FIG. 9, based on the donor's weight and hematocrit for the initial collection phase, or by any of the other methods as set forth above. Alternatively, the controller is configured to calculate the target plasma product collection volume for the initial collection phase in accordance with a methodology such as those described above upon the operator entering, e.g., the donor's weight and hematocrit, and/or any of the additional donor-specific information (such as the donor's sex, height and age) required by the methodologies used for determining a donor's total blood volume, total plasma volume, and the target volume of harvestable plasma that may be collected.

Preferably, the system administrator will initially set an indication of whether the targeted collection volume of plasma product, TVPP, will be determined by the system (e.g., in accordance with one of the methods described above) or entered directly by the operator into the system. If the operator is to enter the TVPP, then the system administrator will disable the controller's capability to calculate a TVPP. The system administrator will also set an AC ratio to be used for all procedures. If the controller is to determine the TVPP, the administrator will set the system to allow the appropriate donor specific characteristics for calculating the TVPP in accordance with any of the methods described above to be entered into the controller, either by the operator or a donor management system, by which donor parameters used for qualification screening (such as weight, height, and hematocrit) can be electronically sent to the instrument, avoiding operator error in entering the donor parameters. The donor management system could also utilize the donor screening measurements, along with the relationship between pure plasma volume and collection volume, to automatically calculate a TVPP that it would transmit to the controller of the plasmapheresis device. Otherwise, the controller will calculate the TVPP before collection of whole blood form the donor starts. In addition, if the controller/donor management system is to calculate TVPP, the administrator will set the system to enable the operator to enter a TVPP other than the calculated volume. Further, the system will permit the operator to change the TVPP from the calculated TVPP, either before or during the procedure, if, for example, the estimated time for running/completing the procedure needs to be shortened for reasons of donor comfort or convenience. At the completion of the procedure the actual volume of plasma product collected, VPP, and the target volume, TVPP, will be displayed, as well as the actual volume of pure plasma collected and the target volume of plasma, TPV.

As noted above, plasmapheresis procedures may be performed with multiple cycles of collection/draw phases and return/reinfusion phases. If the return/reinfusion phase does not include reinfusion of a replacement fluid, the donor's hematocrit will increase from one cycle to the next. Consequently, if the target volume for plasma product is determined based only on the donor's initial hematocrit, and does not consider the donor's increasing hematocrit, the percentage of anticoagulant in the plasma product will be greater (and the volume of pure plasma less) than what was predicted by the initial calculation for determining the target volume of plasma product. Thus, in order to ensure that the volume of plasma product that is collected contains the maximum volume of raw plasma that was determined to be harvested from a particular donor, the target volume for plasma product is recalculated periodically throughout the plasmapheresis procedure, such as before the start of the collection phase of each cycle, to consider the change in the donor's hematocrit.

Accordingly, after the determination of the target volume for plasma product based on the donor's starting hematocrit is made, the plasmapheresis procedure commences with a first draw phase until a specified volume of whole blood (e.g., approximately 500 ml) has been withdrawn from the donor. Anticoagulant is added to the whole blood and the anticoagulated whole blood is separated into a plasma product, red blood cells, and other non-RBC blood components. At the conclusion of the first draw phase, the red blood cells and non-RBC blood components are returned to the donor. The current volume of plasma product collected after the first draw phase is determined by, e.g., the weigh scale. Then a current value for the hematocrit of the donor is established and a new target volume of plasma product to be collected is determined, and the second cycle of draw and return phases is performed. The cycle of draw and return phases is repeated until the target volume of plasma product for the plasmapheresis procedure is collected, as recalculated prior to the start of each draw phase. After the final collection phase, the controller initiates the final red blood cell reinfusion stage, after which the donor is disconnected.

The benefits of performing a plasmapheresis procedure having multiple collection/reinfusion cycles in accordance with the methodology set forth above may be seen by reference to the tables of FIGS. 10 and 11a, 11b. FIG. 10 displays the input data for a hypothetical plasmapheresis procedure for a donor weighing 190 lbs. (86.4 kg) and having an initial hematocrit of 44. With reference to the table of FIG. 1, the simplified FDA nomogram would limit the volume of plasma to be collected from such a donor to 800 mL, and the total collection volume for the plasma product to 880 mL. In the present example, the FDA nomogram limit on the volume of raw plasma that may be collected is for illustrative purposes only. As set forth above, other methodologies may be used to determine the amount of raw plasma that may be safely extracted from a donor that would differ from that indicated by the FDA nomogram.

The number of collection and reinfusion cycles in a plasmapheresis procedure may vary from three to twelve. In the hypothetical plasmapheresis procedure, there are five collection and reinfusion cycles, which are chosen for illustrative purposes.

Before the commencement of the first collection cycle, the volume of raw plasma to be collected and the total target volume of plasma product to be collected are determined in accordance with the methodologies described above, based on the donor's initial hematocrit. As set forth in the first row of the table (Cycle 1 start), the initial target volume for the plasma product to be collected is 889 mL, which is the same as indicated by the table of FIG. 9 for a donor having a weight of 175 lbs. and up and a hematocrit of 44 in order to harvest the FDA limit of 800 mL of raw plasma from the donor.

During each collection phase, 500 mL of whole blood is drawn from the donor, to which anticoagulant is added at a predetermined ratio (i.e., 1:16), such that 31 mL is added for each collection cycle of 500 mL. The whole blood plus anticoagulant is separated into a plasma fraction and a red blood cell fraction.

During the first return phase (Cycle 1 return end), the red blood cells and "non-RBC" blood components are returned to the donor, so that at the end of the first return cycle the donor's hematocrit has increased to 45.6%, as calculated by the controller based on a blood volume being decreased by the amount of raw plasma collected, while the quantity of red blood cells in the total blood volume remains the same as at the start of the procedure. The controller can also account for the volume of anticoagulant that is reinfused in each return phase along with the red blood cells, as well as the residual anticoagulant in the donor's whole blood being drawn in cycles 2 and following, when determining the new hematocrit value for the next cycle. The volume of raw plasma and the total target volume of plasma product to be collected for the procedure are then recalculated based on the donor's new, increased hematocrit and raw plasma volume. This provides for a new total target collection volume of 891 mL.

The second collection phase is then performed, resulting in a total of 430 mL of plasma product comprising 386 mL of raw plasma being collected over the first two collection phases (Cycle 2 draw end). The red blood cells and "non-RBC" blood components are again returned to the donor, after which the donor's hematocrit is calculated to be 47.2%.

Two more collection phases of 500 mL are performed, each followed by a return phase, in which new values for the volume of raw plasma and total volume of plasma product to be collected are determined before the start of each collection phase. With the increasing hematocrit of the donor, the recalculated target collection volume for procedure increases to 893 mL (for the third collection phase) and then to 894 ml (for the fourth collection phase). A fifth "mini" collection cycle is performed to bring the volume of raw plasma collected up to the 800 mL permitted by the FDA nomogram for the hypothetical donor. The recalculated target collection volume of plasma product for the fifth collection phase remains at 894 mL.

Thus, as illustrated in the example above, when the target collection volume for the plasma product is recalculated for each collection phase, a target collection volume for the plasma product of 894 mL is obtained, which is required in order to collect the target volume of raw plasma of 800 mL. In contrast, 889 mL of plasma product would have been collected if the target collection volume is determined based only on the donor's initial hematocrit, or 880 mL if the target collection volume is based on the simplified FDA nomogram. In both cases, less than the target volume of 800 mL would have been collected.

The greater the accuracy with which the hematocrit of the donor can be determined, both before and during the procedure, the more likely the target volume of plasma product collected will include the maximum volume of raw plasma that can be collected for a particular donor. As described above, the hematocrit of the donor during the procedure is based on the assumptions that 100% of the red blood cells that are withdrawn in each draw cycle are reinfused in each return cycle, along with 100% of the non-RBC cellular products and a volume of anticoagulant. However, it has been determined that during the course of a blood separation procedure, interstitial fluid can shift to the intravascular space, resulting in restoring half of the withdrawn volume. See, Saito et al., *Interstitial fluid shifts to plasma compartment during blood donation*, Transfusion 2013; 53(11):

2744-50. The shifted interstitial fluid is in addition to the red blood cells, non-RBC cellular products, and anticoagulant that are reinfused in each return phase. Thus, accounting for the shift of interstitial fluid would result in a more accurate hematocrit determination, and thus a more accurate determination of the target volume for plasma product that will result in the maximum amount of raw plasma.

The shift of interstitial fluid during plasmapheresis has been substantiated by tracking the level of Immunoglobulin G (IgG) of a donor over the course of a plasmapheresis procedure. See, e.g., Burkhardt et al., *Immunoglobulin G levels during collection of large volume plasma for fractionation*; Transfusion 2017; 56:417-420. If there were no shifting of interstitial fluid, the IgG level of the donor would be stable over the course of the plasmapheresis procedure. However, the IgG level has been shown to drop, and the amount that the IgG level drops is a function of the volume of interstitial fluid that has shifted to the blood system.

Figure 12:
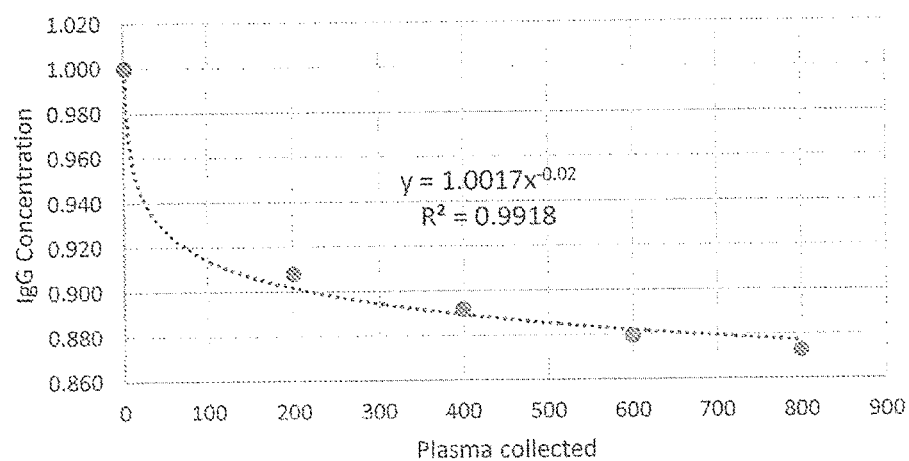
FIG. 12 is a graph illustrating IgG dilution during plasmapheresis.

With reference to FIG. 12, a plot of volume of plasma collected (along the X-axis versus IgG concentration (along the Y-axis) that was developed empirically is shown. A 9% drop of the donor's IgG is seen from the baseline of zero plasma collected (at the start of the procedure) to 200 mL of plasma collected, and a drop of an additional 4% from 200 mL to 800 mL collected. This was attributable to a shift of interstitial fluid equal to approximately 9% of the donor's initial total blood volume (after 200 mL of plasma being collected) to approximately 13% of the donor's initial total blood volume (after 800 mL of plasma being collected).

The following relationship between the amount that the donor's IgG concentration and the volume of plasma collected has been established: $y=1.0017x^{-0.02}$, where y=IgG concentration and x=plasma volume collected. Thus, the percentage of the donor's blood volume that is replaced by the shift of interstitial fluid is equal to $V_b(1-y)$, where $V_b$ is the donor's initial volume of whole blood. Thus, the shifted volume of interstitial fluid can be calculated based on the volume of plasma collected, and this amount can be added to the volume of red blood cells, non-RBC cellular products and anticoagulant reinfused in each return phase to determine the current total blood volume, and thus hematocrit, of the donor. As can be appreciated, the controller can be configured to automatically determine the volume of interstitial fluid that has shifted based on the volume of plasma collected, and to include the shifted volume when determining the donor's hematocrit prior to each draw phase.

Alternatively, other methods that directly measure the donor's hematocrit may be employed, such as an optical sensor or, if a centrifugal separator is being used, measuring the volume of red blood cells in the centrifuge.

In addition, anticoagulant may be introduced into the disposable kit prior to the commencement of the plasmapheresis procedure in pre-processing steps, such as for priming the disposable kit, performing one or more pre-cycles, or for performing other pre-procedure steps. To the extent that anticoagulant used for these purposes is ultimately directed to the plasma product collection container, it may be accounted for in determining the volume contained in the plasma collection container that results in the target volume of raw plasma being collected. This may be done, for example, by measuring the weight of the "full" container of anticoagulant and the weight of the container of anticoagulant prior to the commencement of the first draw cycle, and adding that volume of anticoagulant to the target volume of plasma product. The controller can be configured to automatically perform the steps necessary to account for the anticoagulant introduced into the plasma collection container separately from the anticoagulated plasma.

The methods and system set forth above have several aspects. In a first aspect, a method for collecting plasma in which plasma product is collected in multiple collection phases between which separated red blood cells are reinfused to the donor is provided. The method of this first aspect comprises a) determining a volume of whole blood ($V_b$) and hematocrit (Hct) for a donor; b) determining a volume of raw plasma ($V_{RP}$) that may be collected from the donor; c) determining a volume of plasma product ($V_{PP}$) that may be collected, wherein the plasma product comprises the raw plasma volume plus a volume of anticoagulant; d) withdrawing whole blood from the donor; e) introducing anticoagulant into the withdrawn whole blood at a specified ratio (ACR); f) separating the withdrawn whole blood into a plasma product and a second component comprising red blood cells; g) collecting the plasma product in a plasma collection container; h) after a desired amount of whole blood has been withdrawn from the donor, returning the red blood cells to the donor; and i) determining the Hct of the donor and $V_{PP}$ prior to each collection phase.

In a second aspect, steps d)-i) are continued until a measured volume of plasma product in the collection container equals $V_{PP}$.

In a third aspect, a method for collecting plasma in which plasma product is collected in multiple collection phases between which separated red blood cells are reinfused to the donor is provided. The method of this second aspect comprises: a) determining a volume of whole blood ($V_b$) and hematocrit (Hct) for a donor; b) determining a volume of raw plasma ($V_{RP}$) that may be collected from the donor based on $V_b$; c) determining a volume of anticoagulant $V_{AC}$ to be added to the $V_{RP}$ based on an anticoagulant ratio (ACR) and the Hct of the donor, such that $V_{AC}=V_{RP}*(ACR*(1-Hct))$; d) determining a volume of plasma product ($V_{PP}$) that may be collected, wherein the plasma product comprises the raw plasma volume ($V_{RP}$) plus the volume of anticoagulant ($V_{AC}$); e) withdrawing whole blood from the donor; f) introducing anticoagulant into the withdrawn whole blood at the specified ratio (ACR); g) separating the withdrawn whole blood into a plasma product and a second component comprising red blood cells; h) collecting the plasma product in a plasma collection container; i) after a desired amount of whole blood has been withdrawn from the donor, returning the red blood cells to the donor; and j) determining the Hct of the donor and $V_{PP}$ prior to each collection phase.

In a fourth aspect, steps d)-j) are continued until a measured volume of plasma product in the collection container equals $V_{PP}$.

In a fifth aspect, $V_b$ is determined based on one or more donor specific characteristics including a donor's weight, height, sex, age, and morphology.

In a sixth aspect, a method is provided for collecting a volume of plasma product ($V_{PP}$) in an apheresis procedure in which plasma product is collected in multiple collection phases between which separated red blood cells are reinfused to the donor. In the method of this fourth aspect, $V_{PP}$ is equal to a volume of raw plasma ($V_{RP}$) that may be collected from a donor plus a volume of anticoagulant ($V_{AC}$) that is added to the $V_{RP}$ during the apheresis procedure. The steps of the method comprise: a) determining a weight ($W_{kg}$) and sex (M or F) for the donor; b) determining a hematocrit (Hct) for the donor; c) determining the volume of raw plasma ($V_{RP}$) that may be collected based on the weight ($W_{kg}$) and sex (M or F) of the donor; d) determining a ratio K between the $V_{PP}$ and the $V_{RP}$, such that $K=V_{PP}/V_{RP}$, based on an anticoagulant ratio and the Hct of the donor; e) determining $V_{PP}$, such that $V_{PP}=V_{RP}*K$; f) withdrawing whole blood from the donor; g) introducing anticoagulant into the withdrawn whole blood at a specified ratio (ACR); h) separating the withdrawn whole blood into a plasma product and a second component comprising red blood cells; i) collecting the plasma product in a plasma collection container; j) after a desired amount of whole blood has been withdrawn from the donor, returning the red blood cells to the donor; and k) determining the Hct of the donor and the target $V_{PP}$ prior to each collection phase.

In a seventh aspect, steps c)-k) are repeated until a measured volume of plasma product in the collection container equals $V_{PP}$. Preferably, $K=V_{PP}/V_{RP}=(ACR*(1-Hct/100)+1)/(ACR*(1-HCT/100))$.

In an eighth aspect, a method is provided for collecting a volume of plasma product ($V_{PP}$) in an apheresis procedure in which plasma product is collected in multiple collection phases between which separated red blood cells are reinfused to the donor. In this fifth aspect $V_{PP}$ is equal to a volume of raw plasma ($V_{RP}$) that may be collected from a donor plus a volume of anticoagulant ($V_{AC}$) that is added to the $V_{RP}$ during the apheresis procedure. The steps of the method comprise: a) determining a weight (Wo) and sex (M or F) for the donor; b) determining a hematocrit (Hct) for the donor; c) determining the volume of raw plasma ($V_{RP}$) that may be collected based on the weight of the donor ($W_{kg}$) and the sex (M or F) of the donor; d) determining the $V_{AC}$ to be added to the $V_{RP}$ based on an anticoagulant ratio (ACR) and the Hct of the donor, such that $V_{AC}=V_{RP}*(ACR*(1-Hct))$; e) determining $V_{PP}$, such that $V_{PP}=V_{RP}+V_{AC}$; f) withdrawing whole blood from the donor; g) introducing anticoagulant into the withdrawn whole blood at a specified ratio (ACR); h) separating the withdrawn whole blood into a plasma product and a second component comprising red blood cells; i) collecting the plasma product in a plasma collection container; j) after a desired amount of whole blood has been withdrawn from the donor, returning the red blood cells to the donor; and k) determining the Hct of the donor and $V_{PP}$ prior to each collection phase.

In a ninth aspect, steps d)-k) are continued until a measured volume of plasma product in the collection container equals $V_{PP}$.

In a tenth aspect, $V_{RP}$ is determined by establishing the $V_{RP}$ for each of a plurality of ranges of donor weight, and selecting the $V_{RP}$ for the range of weight that is inclusive of the weight of the donor. The ranges of donor weight may be in three categories from 110 to 149 lbs., 150 to 174 lbs., and 175 lbs. and up.

In an eleventh aspect, $V_{RP}=K_1*W_{kg}$.

In a twelfth aspect, $V_{RP}$ is no greater than 28.6% of $(1-Hct)*(V_b)$.

In a thirteenth aspect, $V_b$ is determined using one of Nadler's equations, Gilcher's Rule of Five, the standards of the ICSH, and any other generally accepted methodology.

In a fourteenth aspect, $V_{RP}=W_{kg}*10$ mL/kg.

In a fifteenth aspect, when donor parameters are used to estimate a total blood volume ($V_b$) for the donor, $V_{RP}=K_2*V_b$.

In a sixteenth aspect, an automated system for separating plasma from whole blood is provided comprising a reusable hardware component and a disposable kit. The disposable kit further comprises i) a separator for separating whole blood into a plasma fraction and a concentrated cell fraction, the separator having an input having a blood line integrally connected thereto for transporting whole blood from a donor to the separator, a plasma output port integrally connected to a plasma collection container by a plasma line, and a concentrated cell outlet port integrally connected to a reservoir for receipt of concentrated cells prior to reinfusion to the donor; ii) a donor line terminating in a venipuncture needle for transporting whole blood from a donor to the blood line, iii) an anticoagulant line integrally connected to the blood line and configured to be connected to a source of anticoagulant for transporting anticoagulant to the donor line, iv) a saline line configured to be attached to a source of saline for transporting saline to the blood line, and v) a reinfusion line for transporting concentrated cells from the reservoir to the donor line. The reusable hardware component further comprises i) a first peristaltic pump for delivering anticoagulant at a controlled rate into the blood line during a collection phase, ii) a second pump for delivering anticoagulated whole blood to the separator during the collection phase and for returning concentrated cellular components during a reinfusion phase, iii) a third pump for delivering concentrated cellular components from the separator to the reservoir during the collection phase, iv) a clamp associated with each of the blood line, plasma line, reinfusion line and saline line, v) a weigh scale for weighing each of the plasma collection container, the reservoir and the source of anticoagulant, and vi) a programmable controller comprising a touch screen for receiving input from an operator, the programmable controller configured to receive a signal from each of the weigh scales and to automatically operate the first, second and third pumps and the clamps to separate whole blood into a plasma fraction and a concentrated cell fraction during the collection phase and to return concentrated cells to the donor during the reinfusion stage. The programmable controller is further configured to determine the weight of the plasma fraction to be collected in the plasma collection container in accordance with any of the aspects described herein, and to terminate the collection phase upon receiving a signal from the weigh scale for the plasma collection container equal to the weight of the plasma fraction determined by the controller. In determining the target amount for the plasma product to be collected, the controller may be configured to calculate the hematocrit of the donor prior to the collection phase of each cycle. Alternatively, or additionally, the controller may receive a signal from a sensor or the like that is indicative of the donor's hematocrit. Further, the amount of plasma product in the plasma collection container may be determined by, e.g., the weigh scale associated with the plasma collection. In one embodiment, the separator comprises a spinning membrane separator.

It will be understood that the embodiments described are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope of the claims is not limited to the above-description, but is set forth in the following claims.

The invention claimed is:
1. A system for collecting plasma from a donor comprising:
   a) a venipuncture needle for withdrawing whole blood from the donor,
   b) a blood separator for separating the whole blood into a plasma product and a second blood component comprising red blood cells;

c) a donor line coupled to the venipuncture needle for introducing whole blood from the donor to the blood separator;
d) a first pump for controlling flow through the donor line;
e) an anticoagulant line coupled to an anticoagulant source for combining anticoagulant with the whole blood;
f) a second pump for controlling flow through the anticoagulant line;
g) a touchscreen is provided for receiving input from an operator; and
h) a programmable controller configured to: determine a target volume of plasma product to be collected (TVPP) based on a weight of the donor, or based on a weight and height of the donor, and a percentage of anticoagulant in the target volume of plasma product to be collected (% $AC_{TVPP}$) based on a pre-determined anticoagulant ratio (ACR) and a hematocrit (Hct) of the donor, control the system to operate a draw and return cycle to withdraw whole blood from the donor, add anticoagulant to the whole blood at a pre-determined ratio (ACR), separate the anticoagulated whole blood into the plasma product and the second component and to return the second component to the donor, and stop withdrawing whole blood from the donor and initiate a final return of the second blood component when a measured volume of plasma product in a plasma collection container reaches the target volume for plasma product, TVPP.

2. The system of claim 1, wherein the controller is further programmed to calculate i) a target volume of pure plasma product to be collected (TVP) from the weight of the donor and ii) the percentage of anticoagulant in the target volume of plasma product to be collected, % $AC_{TVPP}$, based on the pre-determined anticoagulant ratio, ACR, and the hematocrit, Hct, of the donor, wherein the TVPP=TVP/(1−% $AC_{TVPP}$).

3. The system of claim 2, wherein the controller is further programmed to calculate the target volume of pure plasma to be collected, TVP, as a multiple of the weight of the donor.

4. The system of claim 1, wherein the controller is further programmed to calculate a total blood volume of the donor (TBV) based on the weight and height of the donor, a target volume of pure plasma product to be collected, TVP, as a percentage of the TBV, and the percentage of anticoagulant in the target volume of plasma product to be collected, % $AC_{TVPP}$, based on the pre-determined anticoagulant ratio, ACR, and the hematocrit, Hct, of the donor, wherein the TVPP=TVP/(1−% $AC_{TVPP}$).

5. The system of claim 4, wherein the controller is further programmed to calculate the total blood volume of the donor, TBV, based on the weight and height of the donor to calculate a body mass index for the donor (BMI) such that TBV=70/sqrt (BMI/22), where BMI=Wt/$Ht^2$.

6. The system of claim 4, wherein the controller is further programmed to calculate the total blood volume of the donor (TBV) based on the weight (Wt), height (Ht) and sex (Male or Female) of the donor such that TBV=(0.3669*$Ht^3$)+(0.03219*Wt)+0.6041 for Males and TBV=(0.3561*$Ht^3$)+(0.03308*Wt)+0.1833 for Females, where Ht is in meters and Wt is in kilograms.

7. The system of claim 1, wherein ACR is the ratio of the amount of whole blood to the amount of anticoagulant (ACR=WB/AC), and the controller is further configured to determine the percent of anticoagulant in the target volume of plasma product, % $AC_{TVPP}$, such that % $AC_{TVPP}$=1/(1+ACR (1−Hct)).

8. The system of claim 1, wherein ACR is the ratio of volume of whole blood plus the volume of anticoagulant to the volume of anticoagulant (ACR=(WB+AC)/AC), and the controller is further configured to determine the percent of anticoagulant in the target volume of plasma product, % $AC_{TVPP}$, such that % $AC_{TVPP}$=1/(1+(ACR−1)(1−Hct)).

* * * * *